US009289225B2

(12) United States Patent
Shelton, IV et al.

(10) Patent No.: US 9,289,225 B2
(45) Date of Patent: Mar. 22, 2016

(54) ENDOSCOPIC SURGICAL INSTRUMENT WITH A HANDLE THAT CAN ARTICULATE WITH RESPECT TO THE SHAFT

(75) Inventors: Frederick E. Shelton, IV, Hillsboro, OH (US); Jeffrey S. Swayze, Hamilton, OH (US); Mark S. Ortiz, Milford, OH (US); Leslie M. Fugikawa, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 1137 days.

(21) Appl. No.: 12/820,820

(22) Filed: Jun. 22, 2010

(65) Prior Publication Data

US 2010/0305552 A1 Dec. 2, 2010

Related U.S. Application Data

(62) Division of application No. 11/343,547, filed on Jan. 31, 2006, now Pat. No. 7,753,904.

(51) Int. Cl.
*A61B 17/28* (2006.01)
*A61B 17/072* (2006.01)
*A61B 17/29* (2006.01)

(52) U.S. Cl.
CPC ....... *A61B 17/2812* (2013.01); *A61B 17/07207* (2013.01); *A61B 2017/291* (2013.01); *A61B 2017/2919* (2013.01)

(58) Field of Classification Search
CPC .......... A61B 2017/2927; A61B 17/29; A61B 19/22; A61B 2017/0046; A61B 2017/2908
USPC ................................. 606/1, 49–52, 205, 206
See application file for complete search history.

(56) References Cited

U.S. PATENT DOCUMENTS

| 66,052 A | 6/1867 | Smith |
|---|---|---|
| 2,214,870 A | 9/1940 | West |

(Continued)

FOREIGN PATENT DOCUMENTS

| CA | 2458946 A1 | 3/2003 |
|---|---|---|
| CA | 2512960 A1 | 1/2006 |

(Continued)

OTHER PUBLICATIONS

European Search Report, Application No. 07250395.6, dated Apr. 12, 2007 (7 pages).

(Continued)

*Primary Examiner* — Aaron Roane

(57) ABSTRACT

A surgical instrument particular suited to endoscopic use is disclosed. Various embodiments include an end effector that is sized to be inserted through a trocar. An elongated shaft assembly is coupled to the end effector and a control handle. The elongated shaft assembly has a distal portion that is adjacent to said effector for insertion into the trocar. The elongated shaft assembly further has a proximal portion that is remote from the distal portion such that the proximal portion protrudes from the trocar when the end effector and distal portion are inserted therethrough. The control handle is articulatably coupled to the proximal portion of said elongated shaft assembly to enable the surgeon to move the handle portion to a more ergonomically comfortable position while carrying out the endoscopic procedure. Various articulation joint embodiments and locking arrangements are disclosed.

24 Claims, 21 Drawing Sheets

(56) References Cited

U.S. PATENT DOCUMENTS

| | | | |
|---|---|---|---|
| 2,853,074 A | 9/1958 | Olson | |
| 3,078,465 A | 2/1963 | Bobrov | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,819,100 A | 6/1974 | Noiles et al. | |
| 4,213,562 A | 7/1980 | Garrett et al. | |
| 4,305,539 A | 12/1981 | Korolkov et al. | |
| 4,331,277 A | 5/1982 | Green | |
| 4,347,450 A | 8/1982 | Colligan | |
| 4,349,028 A | 9/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,442,964 A | 4/1984 | Becht | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,520,817 A | 6/1985 | Green | |
| 4,522,327 A | 6/1985 | Korthoff et al. | |
| 4,527,724 A | 7/1985 | Chow et al. | |
| 4,530,453 A | 7/1985 | Green | |
| 4,565,189 A | 1/1986 | Mabuchi | |
| 4,566,620 A | 1/1986 | Green et al. | |
| 4,573,622 A | 3/1986 | Green et al. | |
| 4,580,712 A | 4/1986 | Green | |
| 4,591,085 A | 5/1986 | Di Giovanni | |
| 4,610,383 A | 9/1986 | Rothfuss et al. | |
| 4,619,262 A | 10/1986 | Taylor | |
| 4,629,107 A | 12/1986 | Fedotov et al. | |
| 4,655,222 A | 4/1987 | Florez et al. | |
| 4,664,305 A | 5/1987 | Blake, III et al. | |
| 4,665,916 A | 5/1987 | Green | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,728,876 A | 3/1988 | Mongeon et al. | |
| 4,729,260 A | 3/1988 | Dudden | |
| 4,752,024 A | 6/1988 | Green et al. | |
| 4,754,909 A | 7/1988 | Barker et al. | |
| 4,767,044 A | 8/1988 | Green | |
| 4,790,225 A | 12/1988 | Moody et al. | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,844,068 A | 7/1989 | Arata et al. | |
| 4,869,414 A | 9/1989 | Green et al. | |
| 4,869,415 A | 9/1989 | Fox | |
| 4,892,244 A | 1/1990 | Fox et al. | |
| 4,938,408 A | 7/1990 | Bedi et al. | |
| 4,941,623 A | 7/1990 | Pruitt | |
| 4,944,443 A | 7/1990 | Oddsen et al. | |
| 5,031,814 A | 7/1991 | Tompkins et al. | |
| 5,040,715 A | 8/1991 | Green et al. | |
| 5,061,269 A | 10/1991 | Muller | |
| 5,065,929 A | 11/1991 | Schulze et al. | |
| 5,071,430 A | 12/1991 | de Salis et al. | |
| 5,083,695 A | 1/1992 | Foslien et al. | |
| 5,084,057 A | 1/1992 | Green et al. | |
| 5,094,247 A | 3/1992 | Hernandez et al. | |
| 5,100,420 A | 3/1992 | Green et al. | |
| 5,116,349 A | 5/1992 | Aranyi | |
| 5,129,570 A | 7/1992 | Schulze et al. | |
| 5,137,198 A | 8/1992 | Nobis et al. | |
| 5,139,513 A | 8/1992 | Segato | |
| 5,158,567 A | 10/1992 | Green | |
| 5,171,247 A | 12/1992 | Hughett et al. | |
| 5,171,249 A | 12/1992 | Stefanchik et al. | |
| 5,188,111 A | 2/1993 | Yates et al. | |
| 5,200,280 A | 4/1993 | Karasa | |
| 5,207,697 A | 5/1993 | Carusillo et al. | |
| 5,211,649 A | 5/1993 | Kohler et al. | |
| 5,221,036 A | 6/1993 | Takase | |
| 5,222,975 A | 6/1993 | Crainich | |
| 5,236,440 A | 8/1993 | Hlavacek | |
| 5,240,163 A | 8/1993 | Stein et al. | |
| 5,258,009 A | 11/1993 | Conners | |
| 5,275,608 A | 1/1994 | Forman et al. | |
| 5,282,806 A | 2/1994 | Haber et al. | |
| 5,282,829 A | 2/1994 | Hermes | |
| 5,304,204 A | 4/1994 | Bregen | |
| 5,330,502 A | 7/1994 | Hassler et al. | |
| 5,339,799 A | 8/1994 | Kami et al. | |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,383,880 A | 1/1995 | Hooven | |
| 5,383,881 A | 1/1995 | Green et al. | |
| 5,389,098 A | 2/1995 | Tsuruta et al. | |
| 5,391,180 A | 2/1995 | Tovey et al. | |
| 5,395,033 A | 3/1995 | Byrne et al. | |
| 5,395,312 A | 3/1995 | Desai | |
| 5,397,324 A | 3/1995 | Carroll et al. | |
| 5,403,312 A | 4/1995 | Yates et al. | |
| 5,405,072 A | 4/1995 | Zlock et al. | |
| 5,405,344 A | 4/1995 | Williamson et al. | |
| 5,409,498 A | 4/1995 | Braddock et al. | |
| 5,413,272 A | 5/1995 | Green et al. | |
| 5,417,361 A | 5/1995 | Williamson, IV | |
| 5,425,745 A | 6/1995 | Green et al. | |
| 5,431,322 A | 7/1995 | Green et al. | |
| 5,431,668 A | 7/1995 | Burbank, III et al. | |
| 5,433,721 A | 7/1995 | Hooven et al. | |
| 5,447,513 A | 9/1995 | Davison et al. | |
| 5,449,365 A | 9/1995 | Green et al. | |
| 5,458,579 A | 10/1995 | Chodorow et al. | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,474,566 A | 12/1995 | Alesi et al. | |
| 5,476,206 A | 12/1995 | Green et al. | |
| 5,476,479 A | 12/1995 | Green et al. | |
| 5,478,003 A | 12/1995 | Green et al. | |
| 5,478,354 A | 12/1995 | Tovey et al. | |
| 5,480,089 A | 1/1996 | Blewett | |
| 5,480,409 A | 1/1996 | Riza | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,505,363 A | 4/1996 | Green et al. | |
| 5,509,596 A | 4/1996 | Green et al. | |
| 5,518,163 A | 5/1996 | Hooven | |
| 5,518,164 A | 5/1996 | Hooven | |
| 5,520,678 A * | 5/1996 | Heckele et al. | 606/1 |
| 5,527,320 A | 6/1996 | Carruthers et al. | |
| 5,529,235 A | 6/1996 | Boiarski et al. | |
| 5,533,581 A | 7/1996 | Barth et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,547,117 A | 8/1996 | Hamblin et al. | |
| 5,553,675 A | 9/1996 | Pitzen et al. | |
| 5,553,765 A | 9/1996 | Knodel et al. | |
| 5,554,169 A | 9/1996 | Green et al. | |

(56) References Cited

U.S. PATENT DOCUMENTS

| | | |
|---|---|---|
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,579,978 A | 12/1996 | Green et al. |
| 5,580,067 A | 12/1996 | Hamblin et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,618,303 A | 4/1997 | Marlow et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A * | 5/1997 | Grant et al. ............... 227/179.1 |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,697,543 A | 12/1997 | Burdorff |
| 5,700,270 A | 12/1997 | Peyser et al. |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |
| 5,747,953 A | 5/1998 | Philipp |
| 5,749,893 A | 5/1998 | Vidal et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,810,811 A | 9/1998 | Yates et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,826,776 A | 10/1998 | Schulze et al. |
| 5,829,662 A | 11/1998 | Allen et al. |
| 5,833,690 A | 11/1998 | Yates et al. |
| 5,833,695 A | 11/1998 | Yoon |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,855,311 A | 1/1999 | Hamblin et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,904,693 A | 5/1999 | Dicesare et al. |
| 5,906,625 A | 5/1999 | Bito et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,931,847 A | 8/1999 | Bittner et al. |
| 5,931,853 A | 8/1999 | McEwen et al. |
| 5,938,667 A | 8/1999 | Peyser et al. |
| 5,941,442 A | 8/1999 | Geiste et al. |
| 5,948,030 A | 9/1999 | Miller et al. |
| 5,951,574 A | 9/1999 | Stefanchik et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,024,741 A | 2/2000 | Williamson, IV et al. |

(56) References Cited

U.S. PATENT DOCUMENTS

| | | | |
|---|---|---|---|
| 6,032,849 A | 3/2000 | Mastri et al. |
| 6,045,560 A | 4/2000 | McKean et al. |
| 6,050,472 A | 4/2000 | Shibata |
| 6,077,286 A | 6/2000 | Cuschieri et al. |
| 6,079,606 A | 6/2000 | Milliman et al. |
| 6,082,577 A | 7/2000 | Coates et al. |
| 6,083,242 A | 7/2000 | Cook |
| 6,086,600 A | 7/2000 | Kortenbach |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,155,473 A | 12/2000 | Tompkins et al. |
| 6,162,208 A | 12/2000 | Hipps |
| 6,171,330 B1 | 1/2001 | Benchetrit |
| 6,202,914 B1 | 3/2001 | Geiste et al. |
| 6,214,028 B1 | 4/2001 | Yoon et al. |
| 6,223,835 B1 | 5/2001 | Habedank et al. |
| 6,228,084 B1 | 5/2001 | Kirwan, Jr. |
| 6,231,565 B1 | 5/2001 | Tovey et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,309,403 B1 | 10/2001 | Minor et al. |
| 6,315,184 B1 | 11/2001 | Whitman |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 | 8/2002 | Wang et al. |
| 6,436,122 B1 | 8/2002 | Frank et al. |
| 6,443,973 B1 | 9/2002 | Whitman |
| 6,471,106 B1 | 10/2002 | Reining |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,517,565 B1 * | 2/2003 | Whitman et al. ............ 606/219 |
| 6,522,101 B2 | 2/2003 | Malackowski |
| 6,535,764 B2 | 3/2003 | Imran et al. |
| 6,550,546 B2 | 4/2003 | Thurler et al. |
| 6,569,171 B2 | 5/2003 | DeGuillebon et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,605,078 B2 | 8/2003 | Adams |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,636,412 B2 | 10/2003 | Smith |
| 6,638,108 B2 | 10/2003 | Tachi |
| 6,644,532 B2 | 11/2003 | Green et al. |
| 6,669,073 B2 | 12/2003 | Milliman et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,695,199 B2 | 2/2004 | Whitman |
| 6,698,643 B2 | 3/2004 | Whitman |
| 6,699,235 B2 | 3/2004 | Wallace et al. |
| 6,705,503 B1 | 3/2004 | Pedicini et al. |
| 6,716,232 B1 | 4/2004 | Vidal et al. |
| 6,716,233 B1 | 4/2004 | Whitman |
| 6,723,087 B2 | 4/2004 | O'Neill et al. |
| 6,729,119 B2 | 5/2004 | Schnipke et al. |
| 6,752,768 B2 | 6/2004 | Burdorff et al. |
| 6,752,816 B2 | 6/2004 | Culp et al. |
| 6,755,338 B2 | 6/2004 | Hahnen et al. |
| 6,769,594 B2 | 8/2004 | Orban, III |
| 6,773,438 B1 | 8/2004 | Knodel et al. |
| 6,783,524 B2 | 8/2004 | Anderson et al. |
| 6,786,382 B1 | 9/2004 | Hoffman |
| 6,786,896 B1 | 9/2004 | Madhani et al. |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,827,712 B2 | 12/2004 | Tovey et al. |
| 6,830,174 B2 * | 12/2004 | Hillstead et al. ............ 227/175.1 |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,874,669 B2 | 4/2005 | Adams et al. |
| 6,877,647 B2 | 4/2005 | Ratcliff et al. |
| 6,905,057 B2 | 6/2005 | Swayze et al. |
| 6,905,497 B2 | 6/2005 | Truckai et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,994,708 B2 | 2/2006 | Manzo |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,018,390 B2 | 3/2006 | Turovskiy et al. |
| 7,032,798 B2 | 4/2006 | Whitman et al. |
| 7,032,799 B2 | 4/2006 | Viola et al. |
| 7,036,680 B1 | 5/2006 | Flannery |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,075,770 B1 | 7/2006 | Smith |
| 7,077,856 B2 | 7/2006 | Whitman |
| 7,080,769 B2 | 7/2006 | Vresh et al. |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,233 B2 | 4/2007 | Wadge |

(56) References Cited

U.S. PATENT DOCUMENTS

| | | |
|---|---|---|
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,238,195 B2 | 7/2007 | Viola |
| 7,241,288 B2 | 7/2007 | Braun |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,481,347 B2 | 1/2009 | Roy |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,559,450 B2 | 7/2009 | Wales et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,631,793 B2 | 12/2009 | Rethy et al. |
| 7,641,093 B2 | 1/2010 | Doll et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,691,098 B2 | 4/2010 | Wallace et al. |
| 7,699,204 B2 | 4/2010 | Viola |
| 7,717,312 B2 | 5/2010 | Beetel |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,934,631 B2 | 5/2011 | Balbierz et al. |
| 7,972,298 B2 | 7/2011 | Wallace et al. |
| 8,108,072 B2 | 1/2012 | Zhao et al. |
| 8,157,153 B2 | 4/2012 | Shelton, IV et al. |
| 8,167,185 B2 | 5/2012 | Shelton, IV et al. |
| 8,172,124 B2 | 5/2012 | Shelton, IV et al. |
| 8,241,271 B2 | 8/2012 | Millman et al. |
| 8,292,155 B2 | 10/2012 | Shelton, IV et al. |
| 2002/0117534 A1 | 8/2002 | Green et al. |
| 2002/0134811 A1 | 9/2002 | Napier et al. |
| 2002/0165541 A1 | 11/2002 | Whitman |
| 2003/0105478 A1 | 6/2003 | Whitman et al. |
| 2003/0130677 A1 | 7/2003 | Whitman et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0111081 A1 | 6/2004 | Whitman et al. |
| 2004/0116952 A1 | 6/2004 | Sakurai et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |

(56) References Cited

U.S. PATENT DOCUMENTS

| | | |
|---|---|---|
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2005/0033357 A1 | 2/2005 | Braun |
| 2005/0059997 A1 | 3/2005 | Bauman et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0131457 A1 | 6/2005 | Douglas et al. |
| 2005/0143759 A1 | 6/2005 | Kelly |
| 2005/0171522 A1 | 8/2005 | Christopherson |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0008787 A1 | 1/2006 | Hayman et al. |
| 2006/0011699 A1 | 1/2006 | Olson et al. |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0180634 A1 | 8/2006 | Shelton, IV et al. |
| 2006/0212069 A1 | 9/2006 | Shelton, IV |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0259073 A1 | 11/2006 | Miyamoto et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0170225 A1 | 7/2007 | Shelton, IV et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0244471 A1 | 10/2007 | Malackowski |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167644 A1 | 7/2008 | Shelton et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314957 A1 | 12/2008 | Boudreaux |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0090763 A1 | 4/2009 | Zemlok et al. |
| 2009/0108048 A1 | 4/2009 | Zemlok et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0209979 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |

(56) References Cited

U.S. PATENT DOCUMENTS

| | | |
|---|---|---|
| 2009/0289096 A1 | 11/2009 | Shelton, IV et al. |
| 2009/0292283 A1 | 11/2009 | Odom |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0144640 A1 | 6/2011 | Heinrich et al. |
| 2011/0155784 A1 | 6/2011 | Shelton, IV et al. |
| 2011/0174862 A1 | 7/2011 | Shelton, IV et al. |
| 2011/0290856 A1 | 12/2011 | Shelton, IV et al. |
| 2011/0295295 A1 | 12/2011 | Shelton, IV et al. |
| 2012/0074196 A1 | 3/2012 | Shelton, IV et al. |
| 2012/0175399 A1 | 7/2012 | Shelton et al. |
| 2012/0199630 A1 | 8/2012 | Shelton, IV |
| 2012/0209289 A1 | 8/2012 | Duque et al. |
| 2012/0292367 A1 | 11/2012 | Morgan et al. |
| 2013/0012957 A1 | 1/2013 | Shelton, IV et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0087597 A1 | 4/2013 | Shelton, IV et al. |
| 2013/0116668 A1 | 5/2013 | Shelton, IV et al. |
| 2013/0116669 A1 | 5/2013 | Shelton, IV et al. |
| 2013/0123822 A1 | 5/2013 | Wellman et al. |
| 2013/0126582 A1 | 5/2013 | Shelton, IV et al. |
| 2013/0181033 A1 | 7/2013 | Shelton, IV et al. |
| 2013/0181034 A1 | 7/2013 | Shelton, IV et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0313303 A1 | 11/2013 | Shelton, IV et al. |
| 2013/0313304 A1 | 11/2013 | Shelton, IV et al. |

FOREIGN PATENT DOCUMENTS

| | | |
|---|---|---|
| CA | 2514274 A1 | 1/2006 |
| DE | 273689 C | 5/1914 |
| DE | 1775926 A | 1/1972 |
| DE | 3210466 A1 | 9/1983 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 81 | 7/1996 |
| EP | 0667119 B1 | 7/1996 |
| EP | 0770355 A1 | 5/1997 |
| EP | 0503662 B1 | 6/1997 |
| EP | 0578425 81 | 9/1997 |
| EP | 0625335 B1 | 11/1997 |
| EP | 0552423 81 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 81 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |

(56) References Cited

FOREIGN PATENT DOCUMENTS

| | | |
|---|---|---|
| EP | 1617768 B1 | 8/2006 |
| EP | 1702567 A2 | 9/2006 |
| EP | 1129665 B1 | 11/2006 |
| EP | 1400206 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| EP | 1769754 B1 | 6/2010 |
| EP | 1702570 B1 | 10/2010 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1993 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/010482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

(56) References Cited

FOREIGN PATENT DOCUMENTS

OTHER PUBLICATIONS

European Examination Report for Application No. 07250395.6, dated Mar. 13, 2009 (4 pages).

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

"U.S. Appl. No. 14/224,878, filed Mar. 25, 2014".

\* cited by examiner

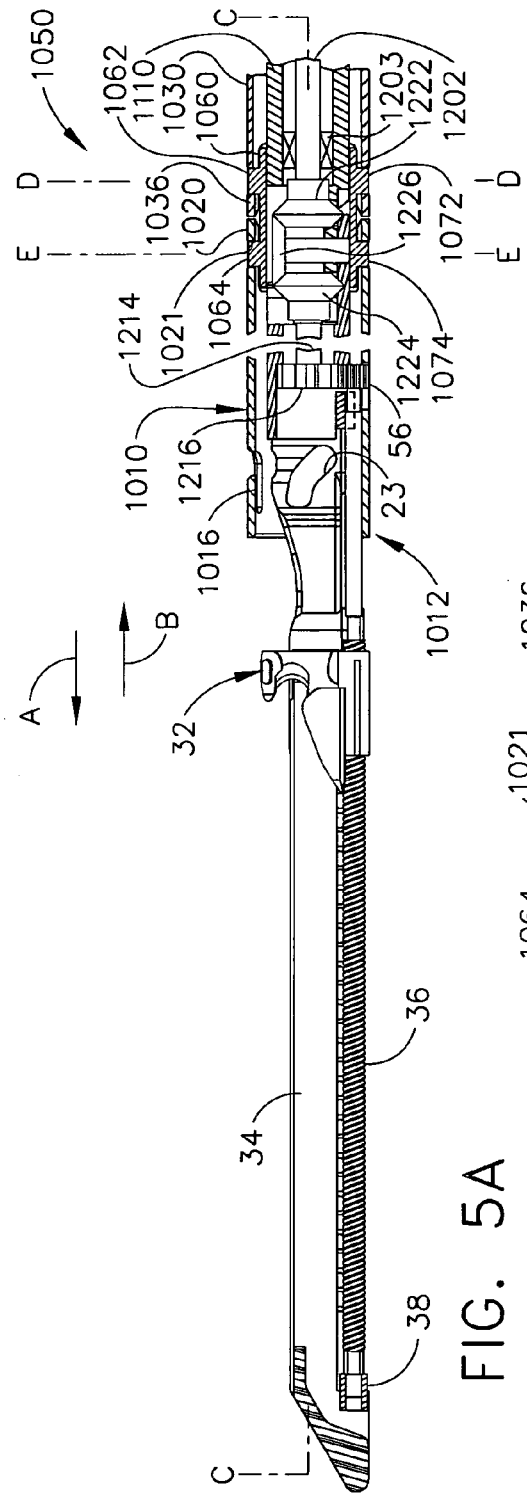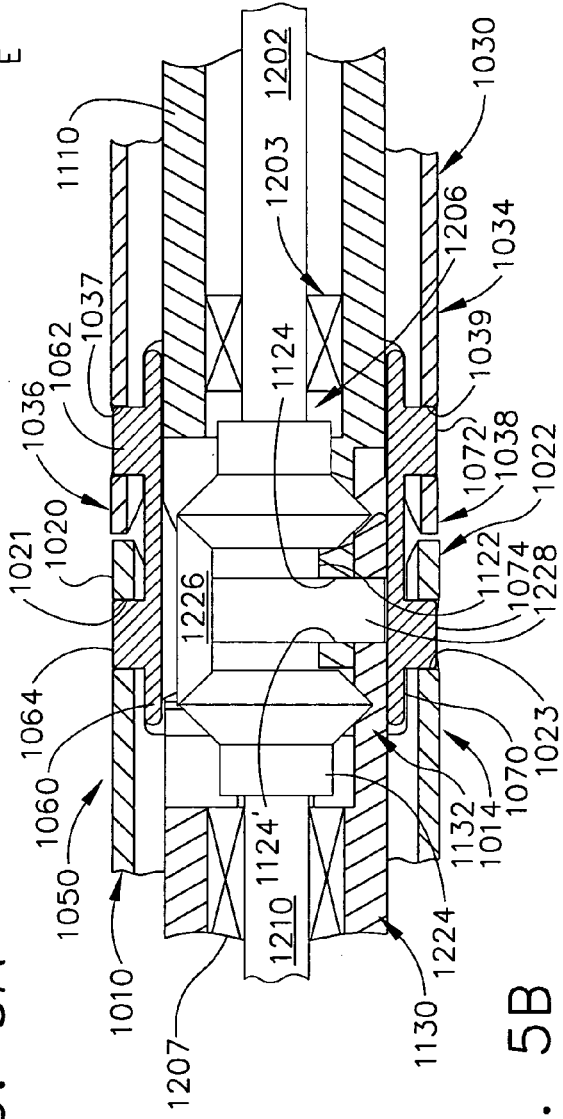

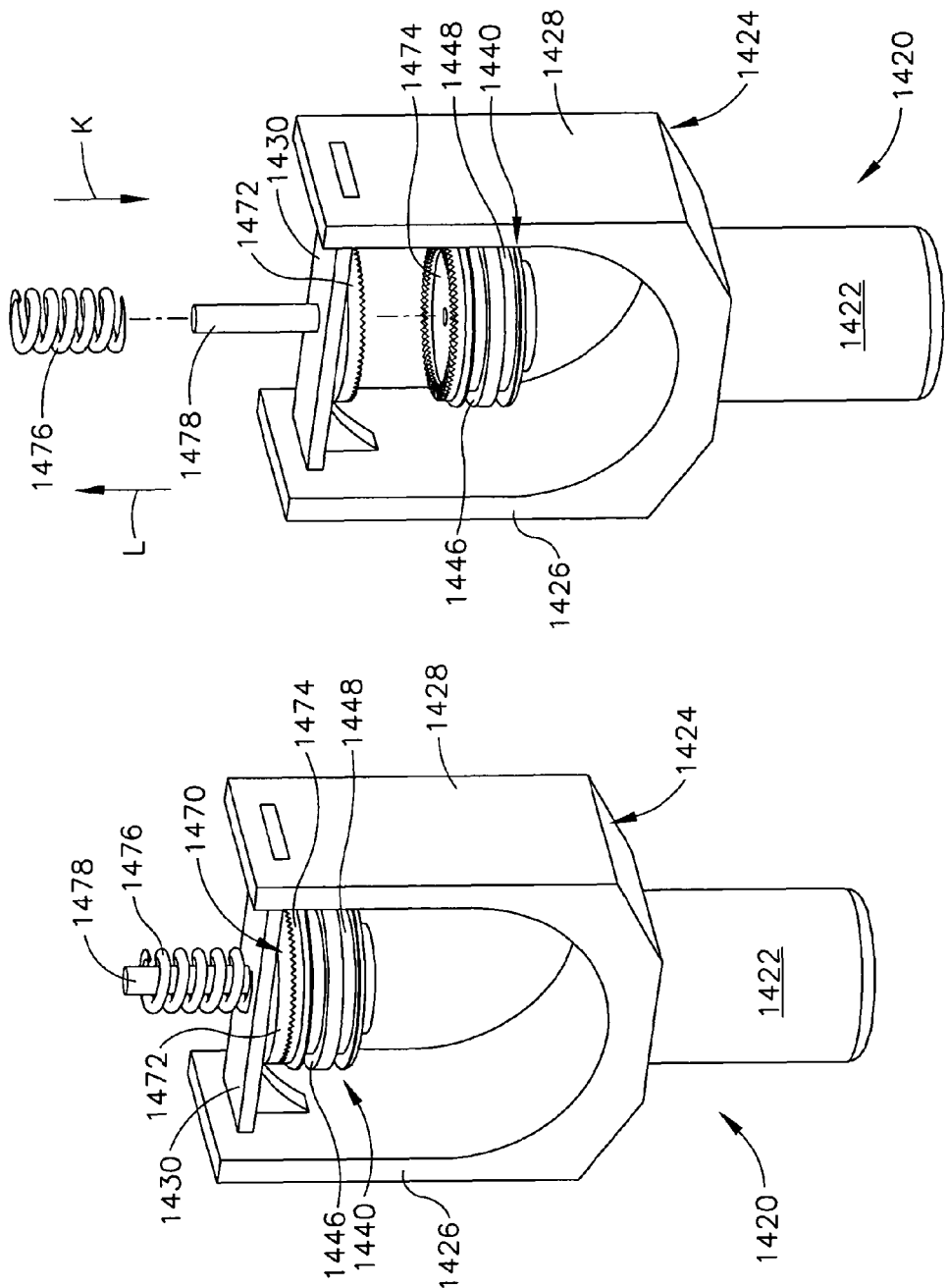

ENDOSCOPIC SURGICAL INSTRUMENT WITH A HANDLE THAT CAN ARTICULATE WITH RESPECT TO THE SHAFT

CROSS-REFERENCE TO RELATED APPLICATIONS

The present application is a divisional application claiming priority under 35 U.S.C. §121 to U.S. patent application Ser. No. 11/343,547, entitled "ENDOSCOPIC SURGICAL INSTRUMENT WITH A HANDLE THAT CAN ARTICULATE WITH RESPECT TO THE SHAFT," filed Jan. 31, 2006, now U.S. Pat. No. 7,753,904, the entire disclosure of which is incorporated by reference herein.

The present application is related to the following U.S. patent applications, which are which are incorporated herein by reference in their entirety:

MOTOR-DRIVEN SURGICAL CUTTING AND FASTENING INSTRUMENT WITH USER FEEDBACK SYSTEM
Inventors: Frederick E. Shelton, IV, John Ouwerkerk and Jerome R. Morgan, U.S. patent application Ser. No. 11/343,498.

MOTOR-DRIVEN SURGICAL CUTTING AND FASTENING INSTRUMENT WITH LOADING FORCE FEEDBACK
Inventors: Frederick E. Shelton, IV, John N. Ouwerkerk, Jerome R. Morgan, and Jeffrey S. Swayze, U.S. patent application Ser. No. 11/343,573.

MOTOR-DRIVEN SURGICAL CUTTING AND FASTENING INSTRUMENT WITH TACTILE POSITION FEEDBACK
Inventors: Frederick E. Shelton, IV, John N. Ouwerkerk, Jerome R. Morgan, and Jeffrey S. Swayze, U.S. patent application Ser. No. 11/344,035.

MOTOR-DRIVEN SURGICAL CUTTING AND FASTENING INSTRUMENT WITH ADAPTIVE USER FEEDBACK
Inventors: Frederick E. Shelton, IV, John N. Ouwerkerk, and Jerome R. Morgan, U.S. patent application Ser. No. 11/343,447.

MOTOR-DRIVEN SURGICAL CUTTING AND FASTENING INSTRUMENT WITH ARTICULATABLE END EFFECTOR
Inventors: Frederick E. Shelton, IV and Christoph L. Gillum, U.S. patent application Ser. No. 11/343,562.

MOTOR-DRIVEN SURGICAL CUTTING AND FASTENING INSTRUMENT WITH MECHANICAL CLOSURE SYSTEM
Inventors: Frederick E. Shelton, IV and Christoph L. Gillum , U.S. patent application Ser. No. 11/344,024.

SURGICAL CUTTING AND FASTENING INSTRUMENT WITH CLOSURE TRIGGER LOCKING MECHANISM
Inventors: Frederick E. Shelton, IV and Kevin R. Doll, U.S. Application Ser. No. 11/343,321.

GEARING SELECTOR FOR A POWERED SURGICAL CUTTING AND FASTENING INSTRUMENT
Inventors: Frederick E. Shelton, IV, Jeffrey S. Swayze, Eugene L. Timperman, U.S. patent application Ser. No. 11/343,563.

SURGICAL INSTRUMENT HAVING RECORDING CAPABILITIES
Inventors: Frederick E. Shelton, IV, John N. Ouwerkerk, and Eugene L. Timperman, U.S. patent application Ser. No. 11/343,803.

SURGICAL INSTRUMENT HAVING A REMOVABLE BATTERY
Inventors: Frederick E. Shelton, IV, Kevin R. Doll, Jeffrey S. Swayze and Eugene Timperman, U.S. patent application Ser. No. 11/344,020.

ELECTRONIC LOCKOUTS AND SURGICAL INSTRUMENT INCLUDING SAME
Inventors: Jeffrey S. Swayze, Frederick E. Shelton, IV, Kevin R. Doll, U.S. patent application Ser. No. 11/343,439.

ELECTRO-MECHANICAL SURGICAL INSTRUMENT WITH CLOSURE SYSTEM AND ANVIL ALIGNMENT COMPONENTS
Inventors: Frederick E. Shelton, IV, Stephen J. Balek and Eugene L. Timperman, U.S. patent application Ser. No. 11/344,021.

DISPOSABLE STAPLE CARTRIDGE HAVING AN ANVIL WITH TISSUE LOCATOR FOR USE WITH A SURGICAL CUTTING AND FASTENING INSTRUMENT AND MODULAR END EFFECTOR SYSTEM THEREFOR
Inventors: Frederick E. Shelton, IV, Michael S. Cropper, Joshua M. Broehl, Ryan S. Crisp, Jamison J. Float, Eugene L. Timperman, U.S. patent application Ser. No. 11/343,546.

SURGICAL INSTRUMENT HAVING A FEEDBACK SYSTEM
Inventors: Frederick E. Shelton, IV, Jerome R. Morgan, Kevin R. Doll, Jeffrey S. Swayze and Eugene Timperman, U.S. patent application Ser. No. 11/343,545.

BACKGROUND

The present invention generally concerns endoscopic surgical instruments and, more particularly, powered endoscopic surgical instruments.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar.

Generally, these endoscopic surgical instruments include an "end effector", a handle assembly and an elongated shaft that extends between the end effector and the handle assembly. The end effector is the portion of the instrument configured to engage the tissue in various ways to achieve a desired diagnostic or therapeutic effect (e.g., endocutter, grasper, cutter, staplers, clip applier, access device, drug/gene therapy delivery device, and energy device using ultrasound, RF, laser, etc.).

The end effector and the shaft portion are sized to be inserted through a trocar placed into the patient. The elongated shaft portion enables the end effector to be inserted to a desired depth and also facilitates some rotation of the end effector to position it within the patient. With judicious placement of the trocar and use of graspers, for instance, through another trocar, often this amount of positioning is sufficient. Surgical stapling and severing instruments, such as those described in U.S. Pat. No. 5,465,895, are examples of an endoscopic surgical instrument that successfully positions an end effector by insertion and rotation.

Depending upon the nature of the operation, it may be desirable to further adjust the positioning of the end effector of an endoscopic surgical instrument. In particular, it is often desirable to orient the end effector at an angle relative to the longitudinal axis of the shaft of the instrument. The transverse or non-axial movement of the end effector relative to the instrument shaft is often conventionally referred to as "articulation". This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. Still other examples of articulatable surgical stapling devices are disclosed in U.S. Pat. Nos. 6,250, 532 and 6,644,532.

Although the above-types of endocutters having articulatable end effectors provide the surgeon with the ability to accurately move and position the end effector within the patient, the position of the endocutter handle is dictated by the position of the portion of the shaft that externally protrudes out of the trocar and which is directly attached to the handle. Thus, the surgeon is unable to move the handle to a more comfortable position. Such arrangements can result in the handle of the instrument being located in a cumbersome position, making it difficult for the surgeon to support and operate the device.

Consequently, a significant need exists for an endocutter that has a handle portion that can be selectively positioned to more ergonomically favorable and comfortable positions relative to the portion of the endocutter that is extending through the trocar into the patient.

SUMMARY

In one general aspect, the present invention is directed to a surgical instrument that comprises an end effector sized to be inserted through a trocar. The surgical instrument includes an elongated shaft assembly that is coupled to the end effector. The elongated shaft assembly has a distal portion that is adjacent to the end effector for insertion into the trocar with the effector and a proximal portion that is remote from the distal portion such that the proximal portion protrudes from the trocar when the end effector and distal portion are inserted therethrough. A control handle is articulatably coupled to the proximal portion of the elongated shaft assembly. A locking assembly may be provided to selectively lock the handle in a desired position relative to the proximal portion of the shaft assembly.

In another general aspect, the present invention is directed to a surgical instrument that comprises an end effector that is sized to be inserted through a trocar. An elongated shaft assembly is coupled to the end effector and has a distal portion that is adjacent to the end effector for insertion into the trocar with the end effector and a proximal portion that is remote from the distal portion such that the proximal portion protrudes from the trocar when the end effector and distal portion are inserted therethrough. The surgical instrument further comprises means for controlling the end effector that is articulatably coupled to the proximal portion of the elongated shaft assembly.

In another general aspect, the present invention is directed to a surgical instrument that comprises an end effector that is sized to be inserted through a trocar. The surgical instrument further comprises a control handle that operably supported at least one drive motor therein. A proximal hollow shaft segment that has a first proximal end is rotatably coupled to the control handle for selective rotation about an elongated shaft axis. The proximal hollow shaft also has a first distal end. The surgical instrument further includes a distal hollow shaft segment that has a second distal end portion that is operably coupled to the end effector for selective actuation thereof by axial movement along the elongated shaft axis. The distal hollow shaft segment has a second proximal end portion that is sized to protrude out of the trocar when the end effector is inserted through the trocar. A first upper tab and a first lower tab protrudes from the first distal end of the proximal hollow shaft segment in spaced relation to each other. A second upper tab and a second lower tab protrudes from the second proximal end of the distal hollow shaft segment in spaced relation to each other. The surgical instrument further comprises an upper double pivot link that is sized to span between the first and second upper tabs. The upper double pivot link has a first upper pin pivotally coupled to the first upper tab and a second upper pivot pin is pivotally coupled to the second upper tab. A lower double pivot link sized to span between the first and second lower tabs has a first lower pin that is pivotally coupled to the first lower tab and a second lower pin that is pivotally coupled to the second lower tab. A proximal spine segment is attached to the control handle and extends through the proximal hollow shaft segment such that it protrudes from the first distal end thereof. A distal spine segment extends through the distal hollow shaft segment and has a proximal end that is adjacent a distal end of the proximal spine segment. The distal spine segment has a distal end that is attached to the end effector and is supported within the distal hollow shaft segment such that the distal hollow shaft segment can be selectively axially moved relative to the distal spine segment. A distal drive shaft portion is operably supported in the distal spine segment and is coupled to an actuator shaft in the end effector. A proximal drive shaft portion is operably coupled to one of the drive motors in the control handle and is operably supported within the proximal spine segment. A drive shaft articulation joint is coupled between the distal drive shaft portion and the proximal drive shaft portion to enable the proximal drive shaft portion to articulate relative to the distal drive shaft portion when the control handle is articulated relative to the distal shaft segment.

DRAWINGS

Various embodiments of the present invention are described herein by way of example in conjunction with the following figures, wherein like numeral may be used to describe like parts and wherein:

FIG. 5A is a cross-sectional view of and end effector and the distal portions of a drive shaft assembly and elongated shaft assembly of various embodiments of the present invention;

FIG. 5B is an enlarged cross-sectional view of the articulation joint of various embodiments of the present invention;

Figure 11:
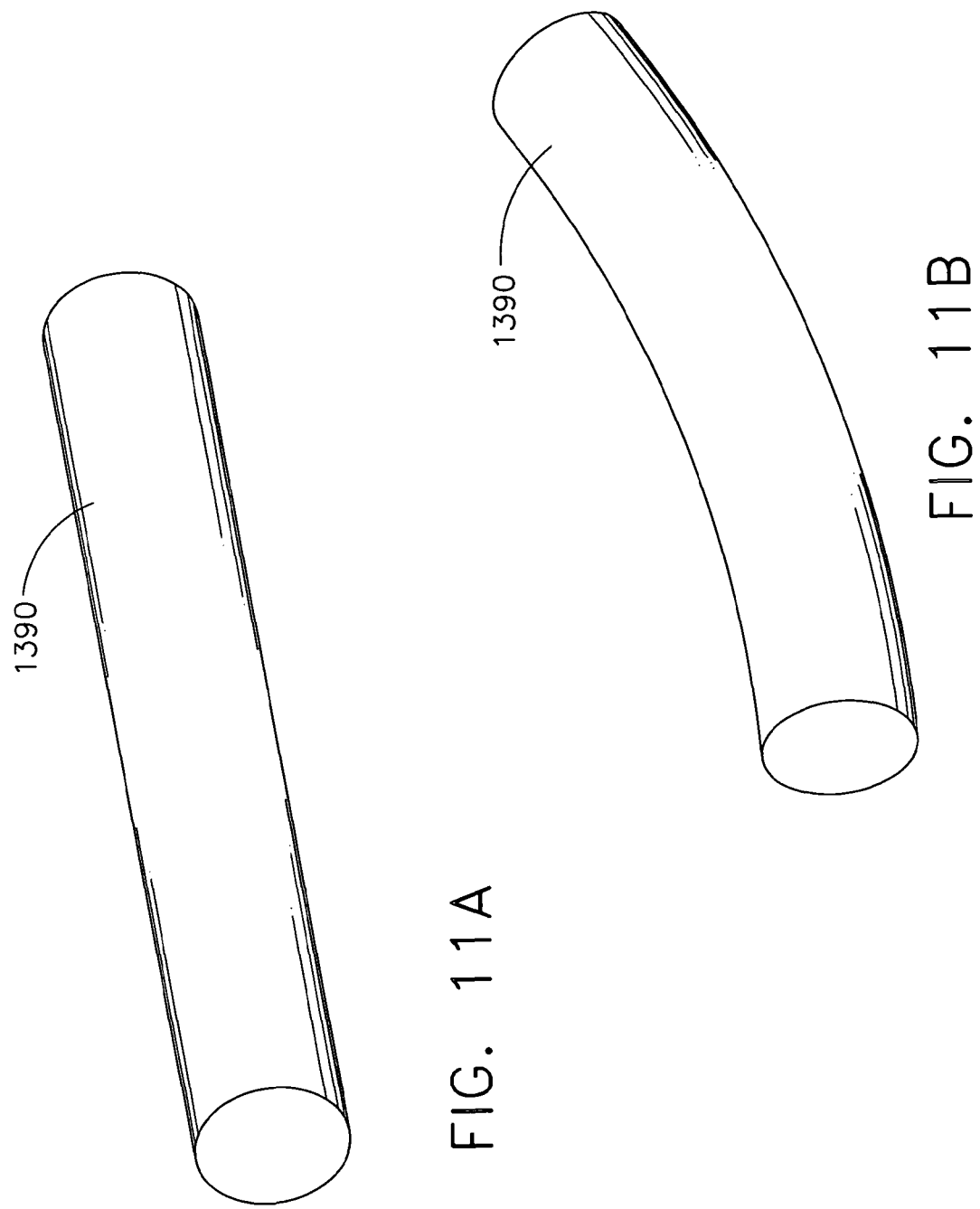
Figure 12:
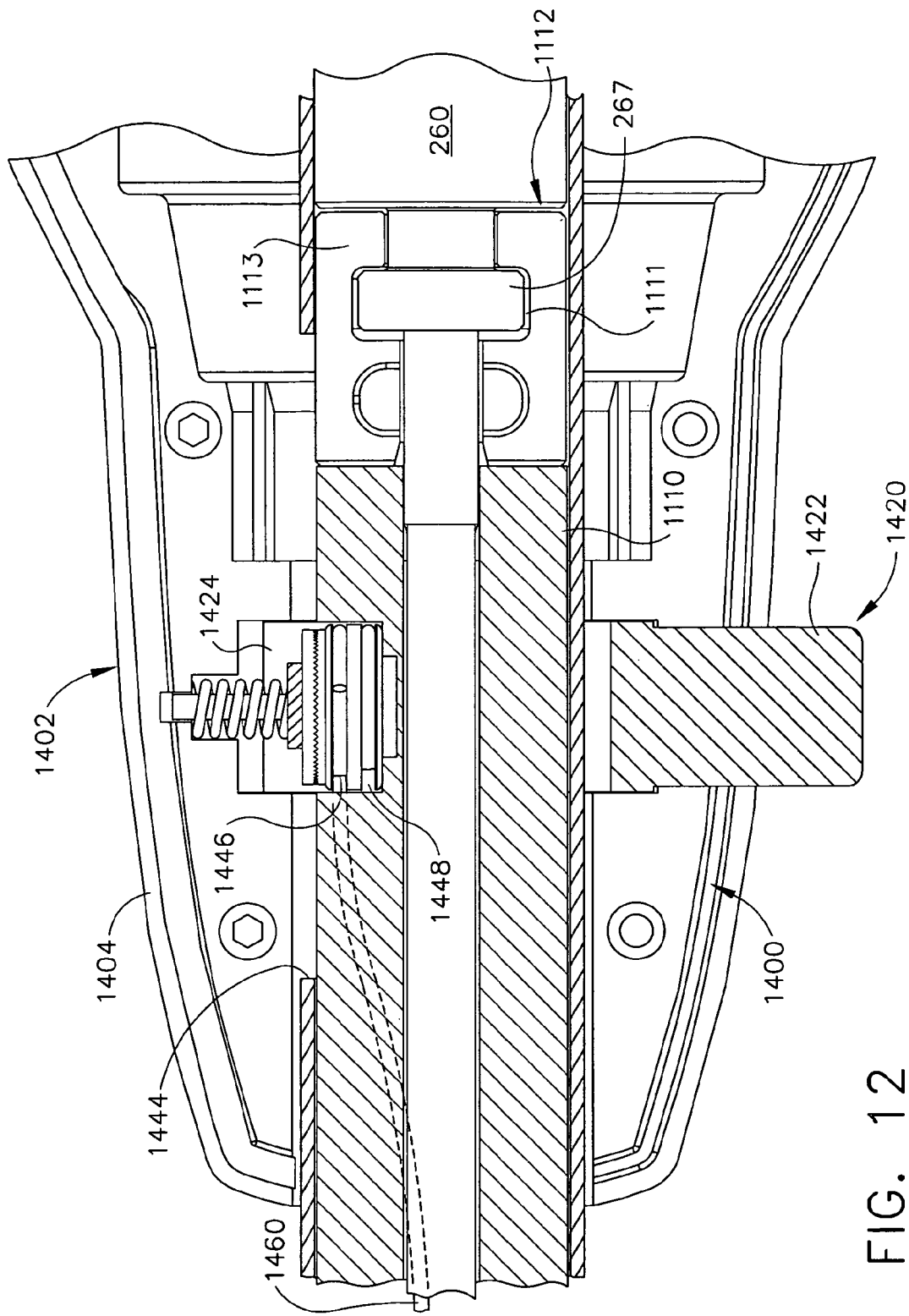
Figure 13:
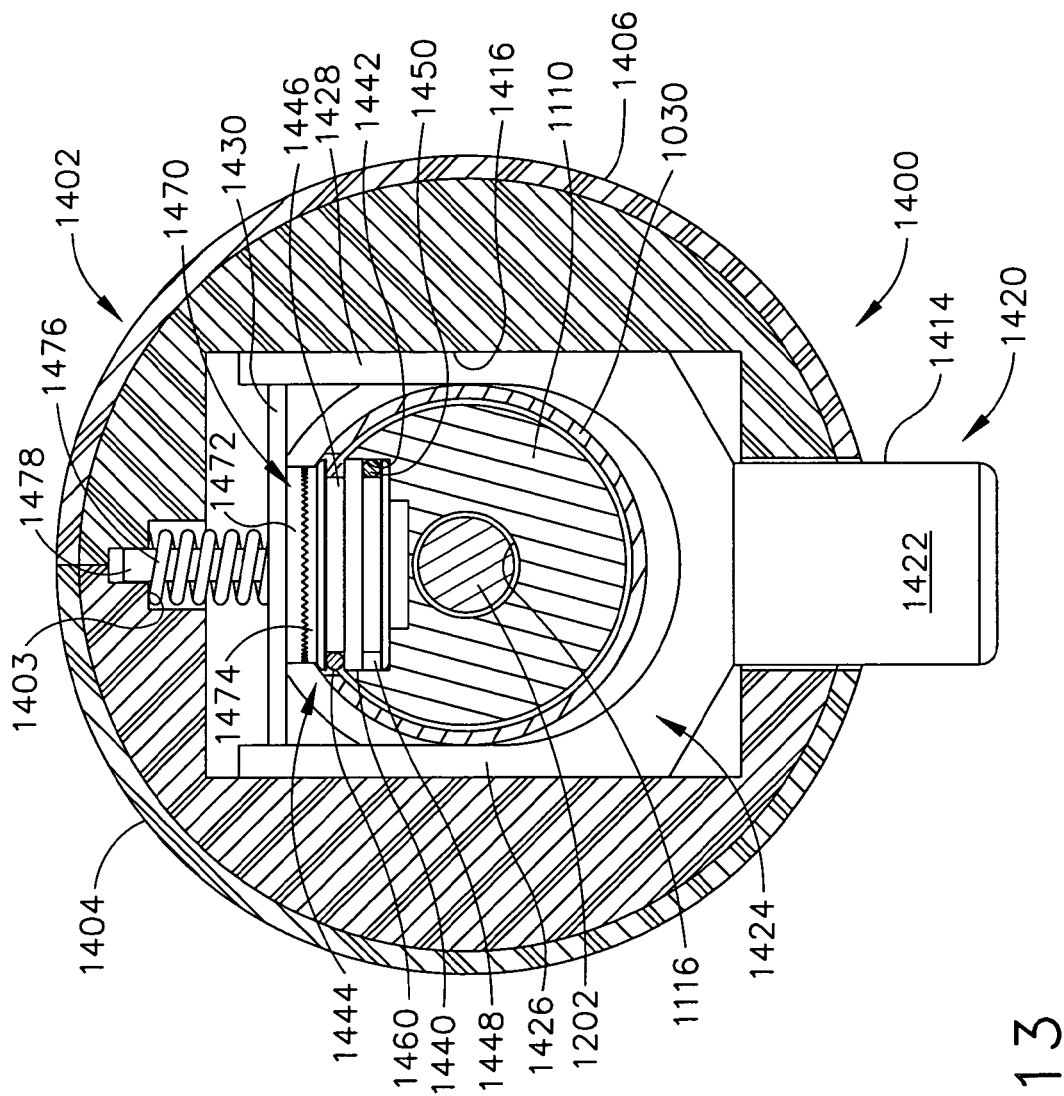
Figure 16:
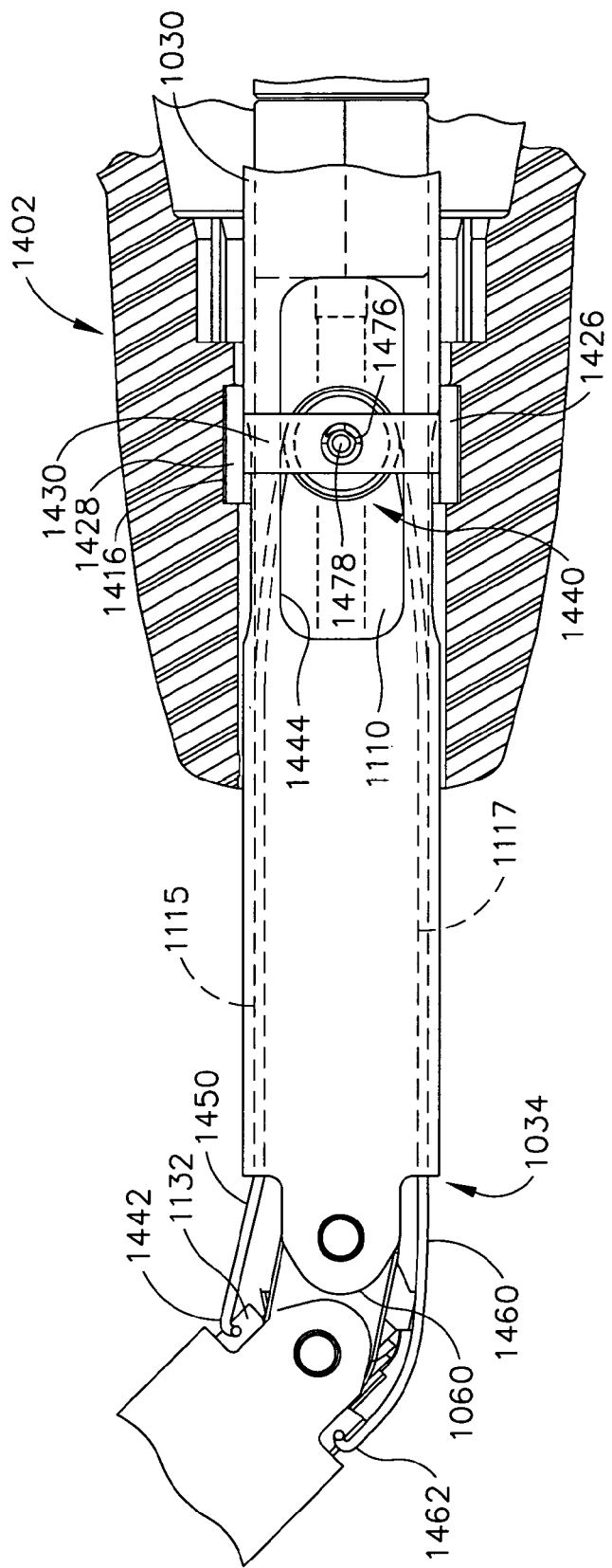
Figure 17:
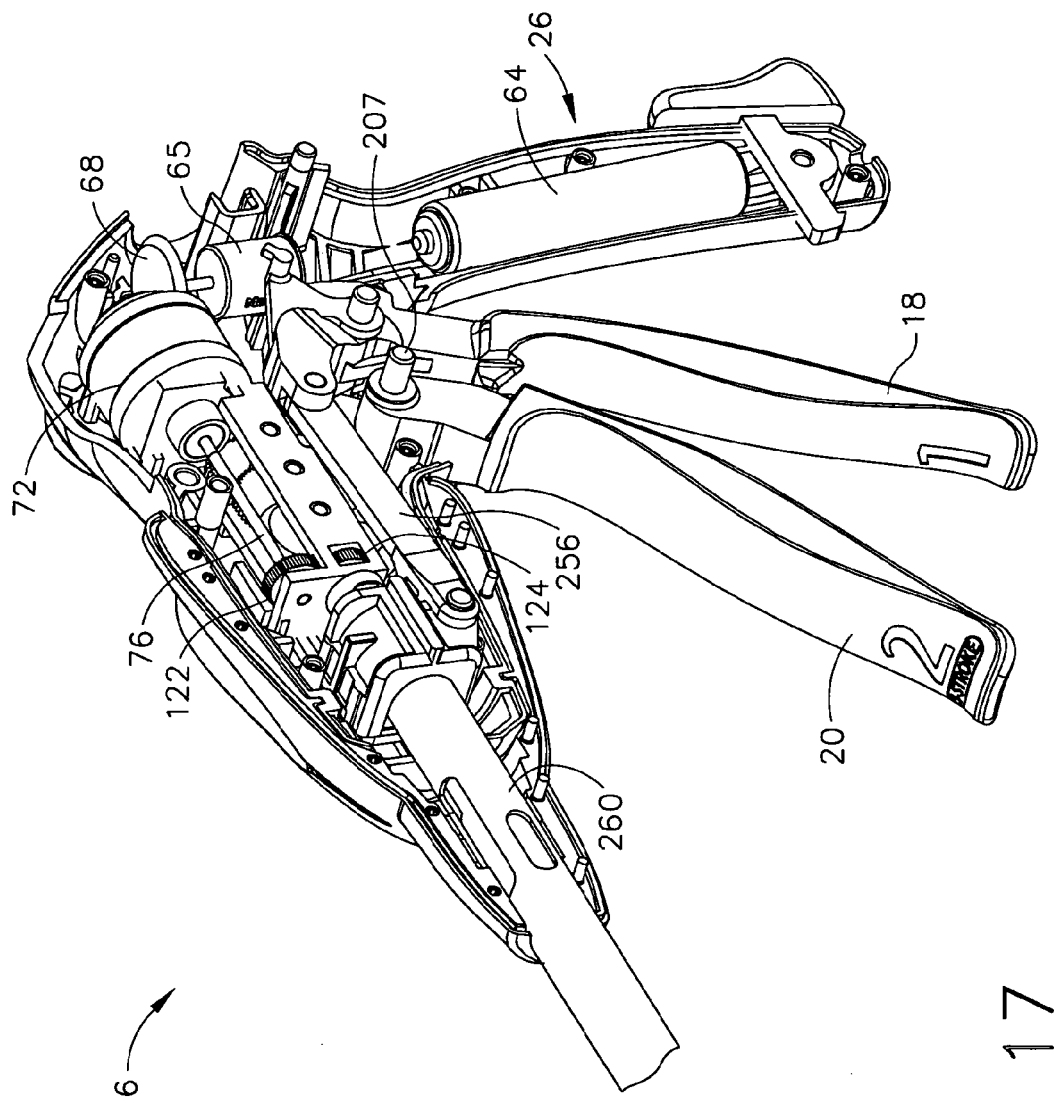
Figure 18:
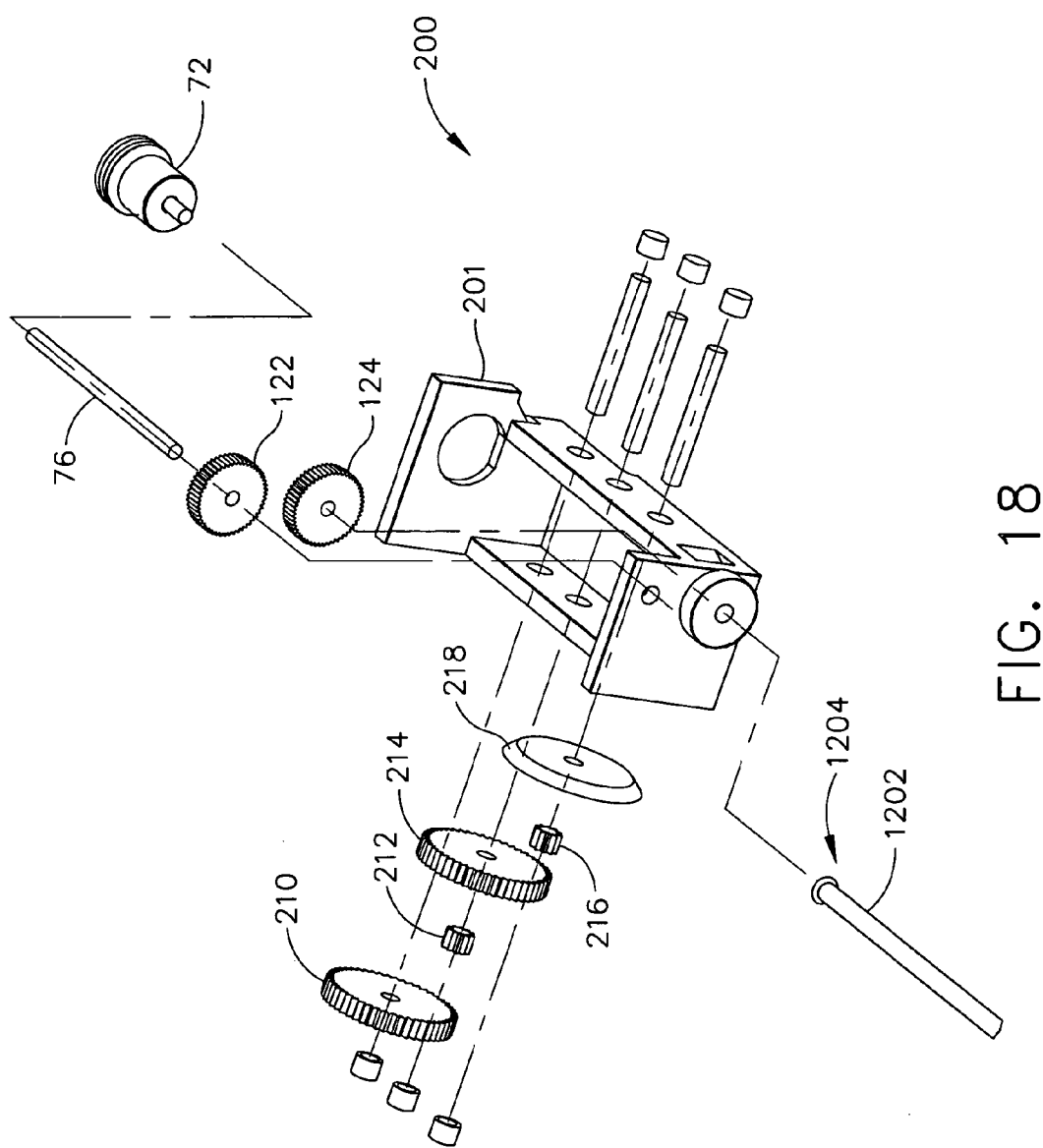
Figure 19:
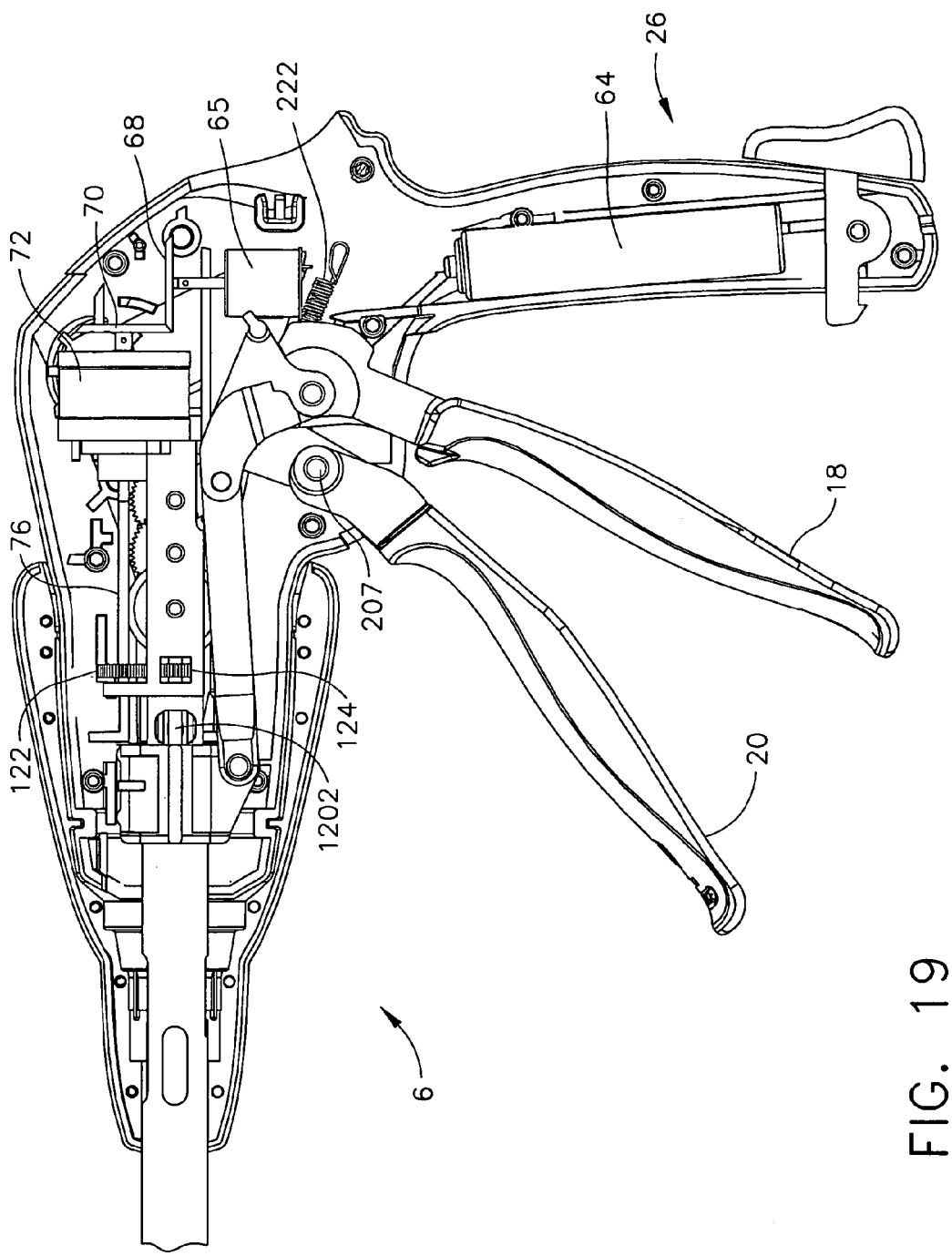
Figure 20:
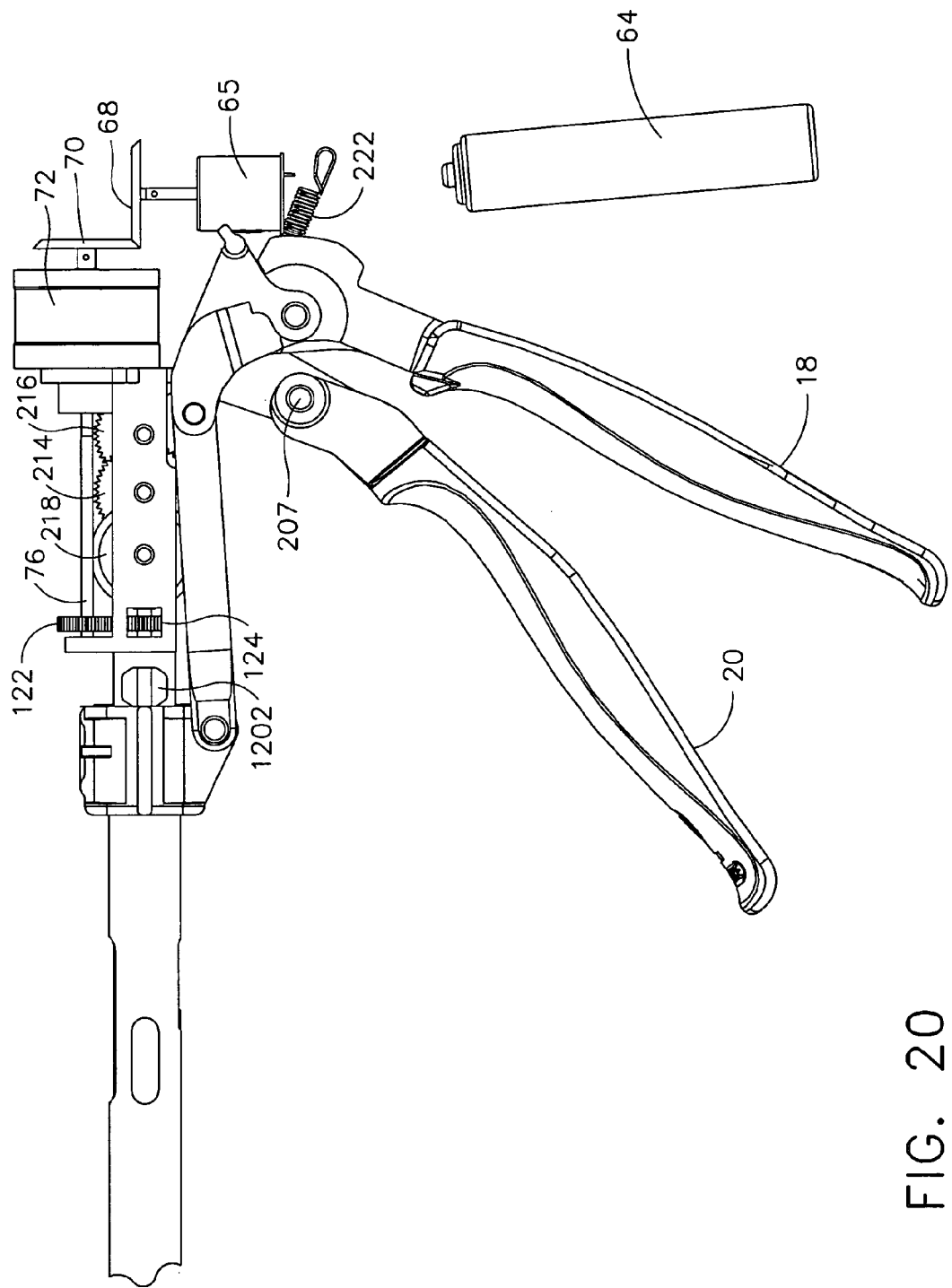
Figure 21:
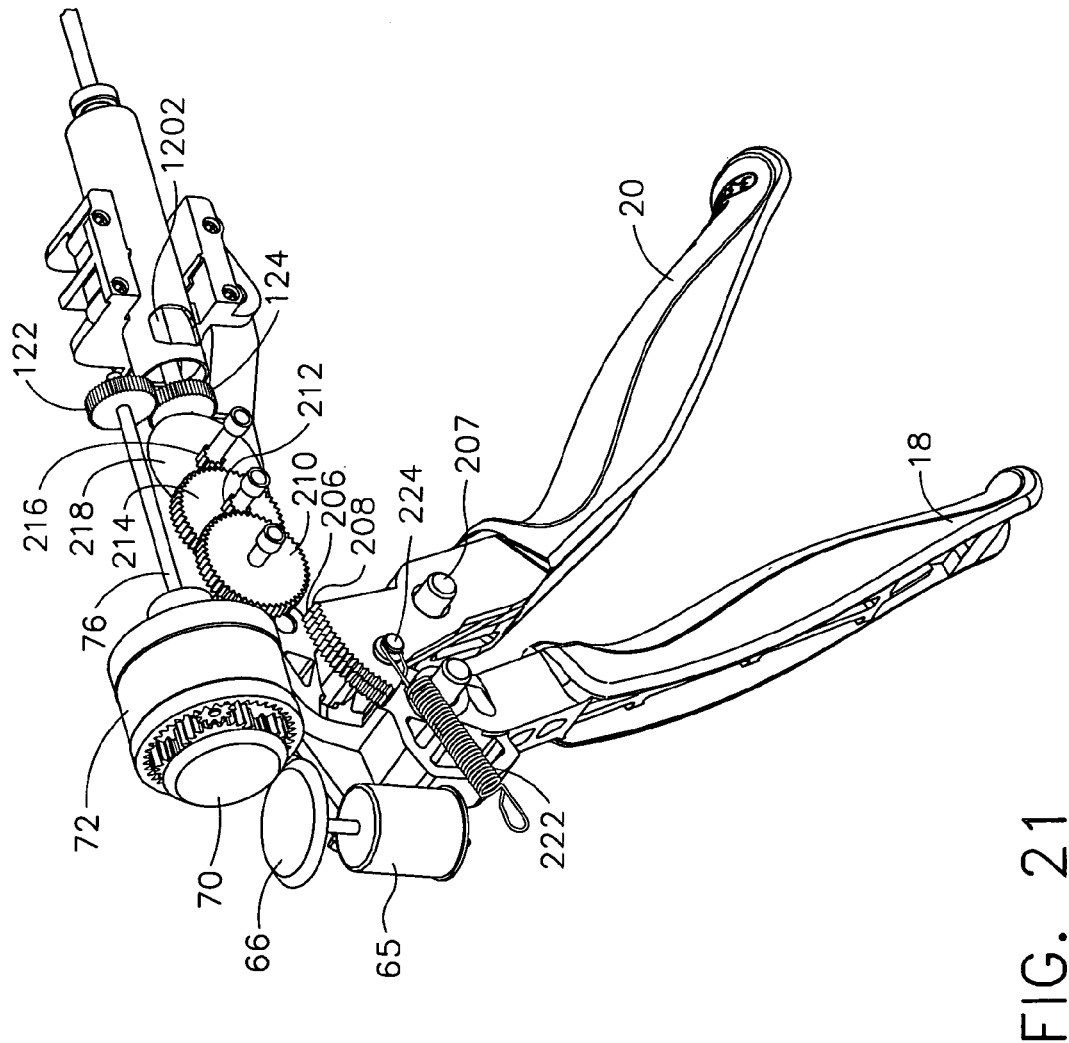
Figure 22:
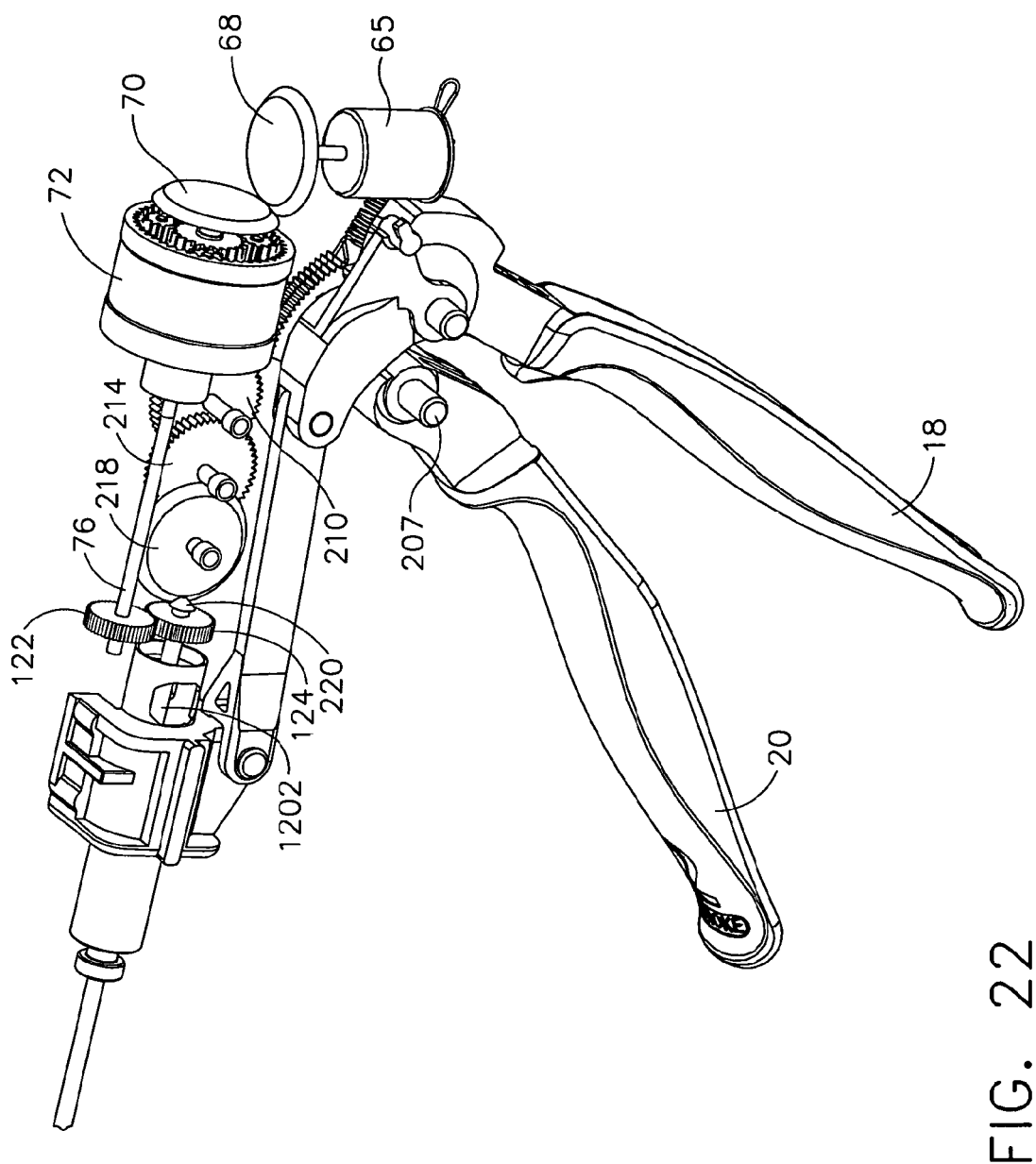

FIGS. 11A-B illustrate a torsion cable that may be employed at the articulation point between the distal and proximal drive shaft portions of various embodiments of the present invention;

FIG. 12 is a partial cross-sectional view of a locking assembly arrangement of various embodiments of the present invention;

FIG. 13 is an end cross-sectional view of the locking assembly arrangement depicted in FIG. 12;

FIG. 14 is a perspective view of a push button assembly of various embodiments of the present invention;

FIG. 15 is an exploded assembly view of the pushbutton assembly of FIG. 14;

FIG. 16 is a partial plan view of a locking assembly arrangement of various embodiments of the present invention, with some of the components shown in cross-section;

FIG. 17 is a front perspective view of a handle assembly that may be employed with various embodiments of the present invention with a portion of the housing removed to illustrate the components therein;

FIG. 18 is an exploded assembly view of a gear arrangement that may be employed in various embodiments of the present invention;

FIG. 19 is a side view of a drive arrangement that may be employed in connection with various embodiments of the present;

FIG. 20 is another side view of the drive arrangement of FIG. 19;

FIG. 21 is a rear perspective view of the drive arrangement of FIGS. 19 and 20; and FIG. 22 is a front perspective view of the drive arrangement of FIGS. 19-21.

DETAILED DESCRIPTION

Figure 1:
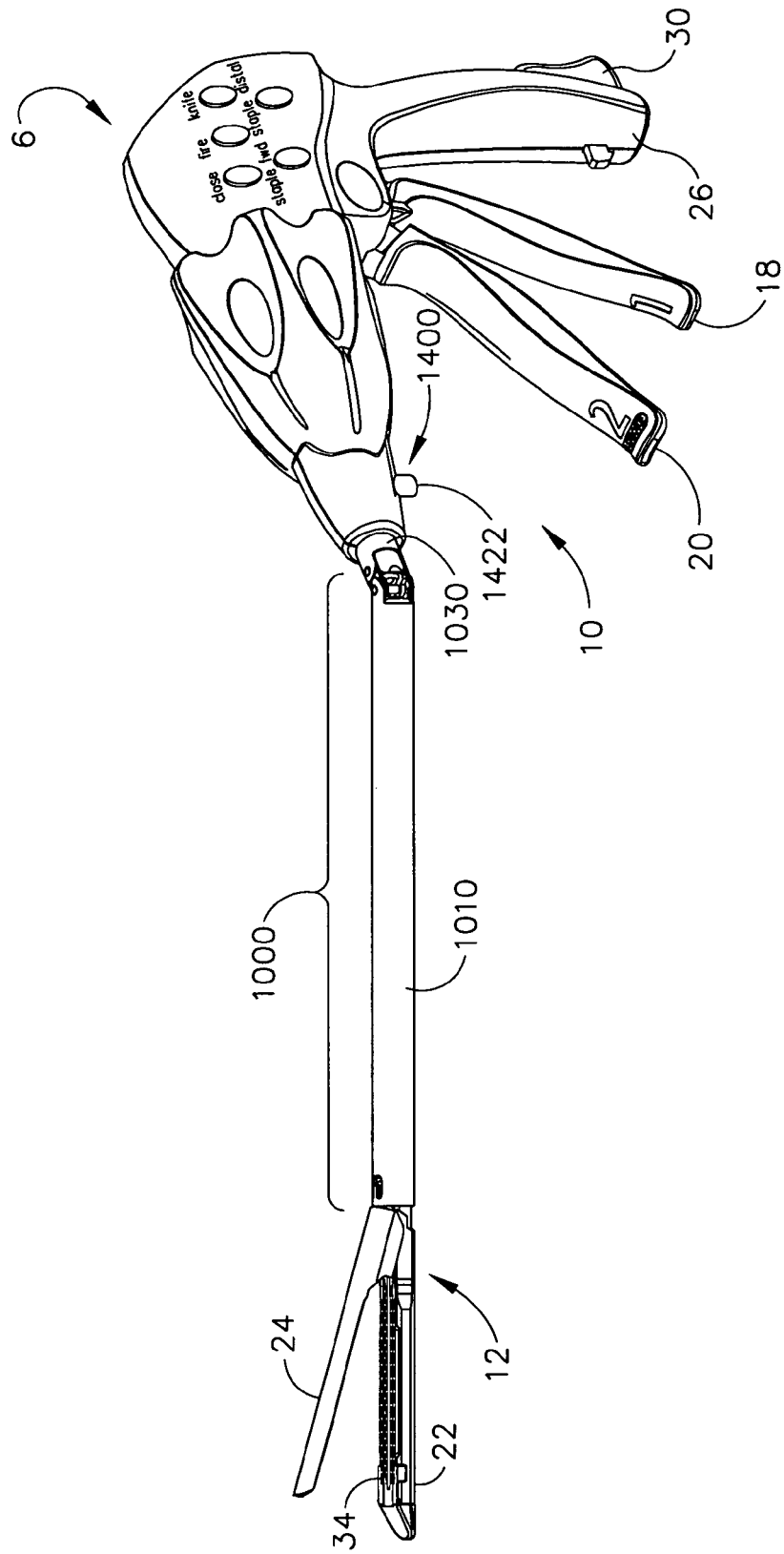
FIG. 1 is a perspective view of a surgical instrument embodiment of the present invention.
Figure 2:
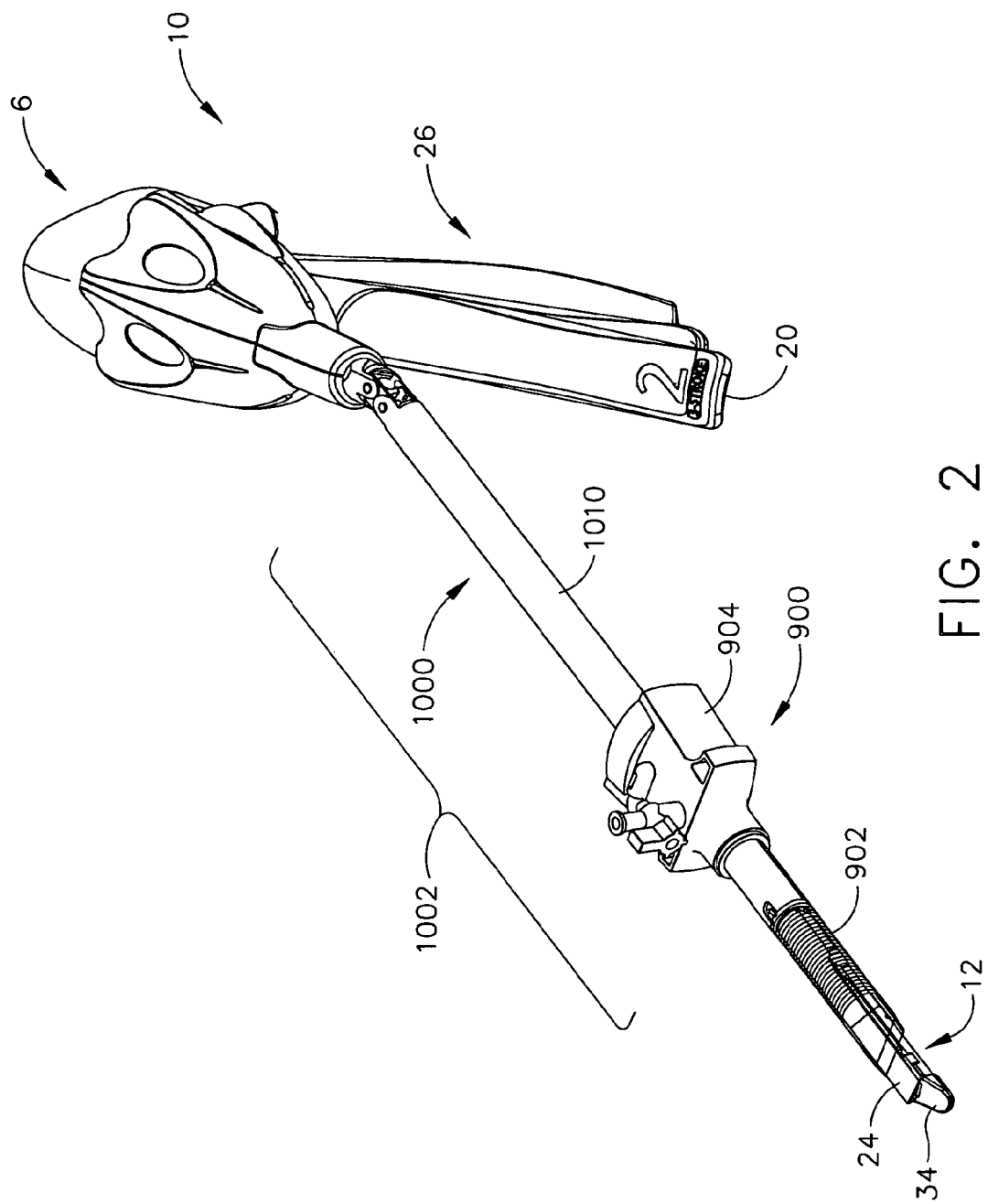
FIG. 2 is another perspective view of the surgical instrument of FIG. 1 with the end effector thereof inserted into a trocar.

FIGS. 1 and 2 depict a surgical stapling and severing instrument 10 that is capable of practicing the unique benefits of the present invention. The surgical stapling and severing instrument 10 comprises a handle 6, an elongated "shaft" or closure tube assembly 1000, and an end effector 12 that is operably coupled to the closure tube assembly 1000. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, etc. While the surgical stapling and severing instrument 10 is depicted as a motor driven or "powered instrument", as the present Detailed Description proceeds, the skilled artisan will appreciate that the unique and novel aspects of the present invention may also be effectively employed in connection with surgical stapling and severing instruments and still other endoscopic surgical instruments that employ mechanical (unpowered) systems for operating the end effector portion thereof without departing from the spirit and scope of the present invention.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating an end effector. The end effector 12 includes in this example, among other things, a staple channel 22 and a pivotally translatable anvil 24, which are maintained at a spacing that assures effective stapling and severing of tissue clamped in the end effector 12. The handle 6 includes a pistol grip 26 toward which a closure trigger 18 is pivotally drawn by the clinician to cause clamping or closing of the anvil 24 toward the staple channel 22 of the end effector 12. The firing trigger 20 is farther outboard of the closure trigger 18. Once the closure trigger 18 is locked in the closure position as further described below, the firing trigger 20 may be pivotally drawn by the clinician to cause the stapling and severing of clamped tissue in the end effector 12.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button 30 on the handle 6, and in this example, on the pistol grip 26 of the handle, when depressed may release the locked closure trigger 18.

Figure 3:
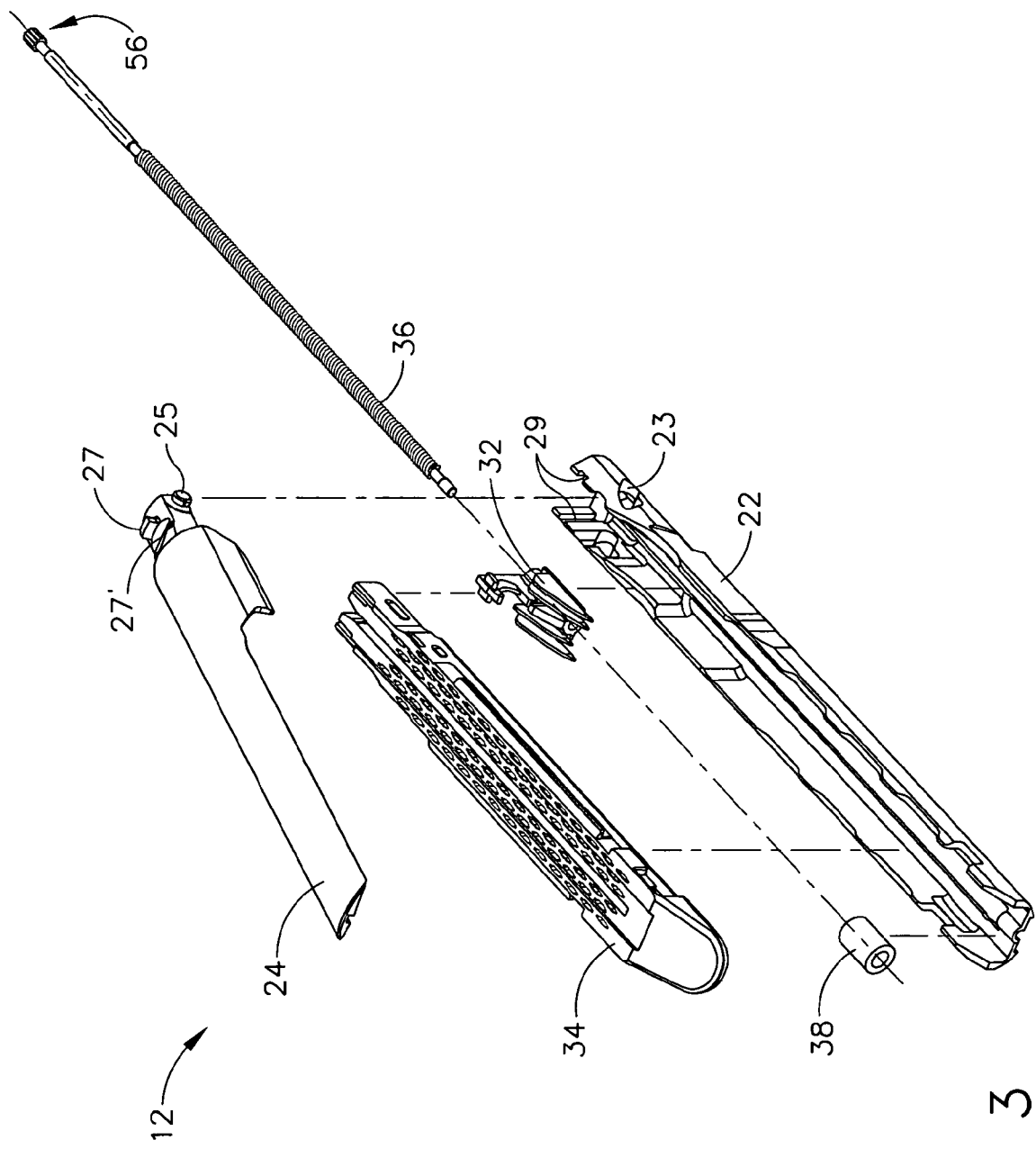
FIG. 3 is an exploded assembly view of an end effector embodiment of the present invention.

FIG. 3 is an exploded view of one end effector 12 according to various embodiments. As shown in the illustrated embodiment, the end effector 12 may include, in addition to the previously mentioned channel 22 and anvil 24, a knife and sled driving member 32, a staple cartridge 34, a helical screw shaft 36 and a bearing 38 that is attached to the channel structure 22. The anvil 24 may be pivotably connected to the channel 22 at a proximate pivot point. In one embodiment, for example, the anvil 24 includes laterally projecting pivot pins 25 at its proximal end that pivotally engage pivot apertures 23 formed near the proximal end of the channel 22. As will be discussed in further detail below, when the closure trigger 18 is actuated, that is, drawn in by a user of the instrument 10, the pivot pins 25 of the anvil 24 may pivot within the pivot apertures 23 in the channel 22 about the pivot point into the clamped or closed position. If clamping of the end effector 12 is satisfactory, the operator may actuate the firing trigger 20, which, as explained in more detail below, causes the knife/ sled driving member 32 to travel along the channel 22, thereby cutting tissue clamped within the end effector 12.

Figure 4:
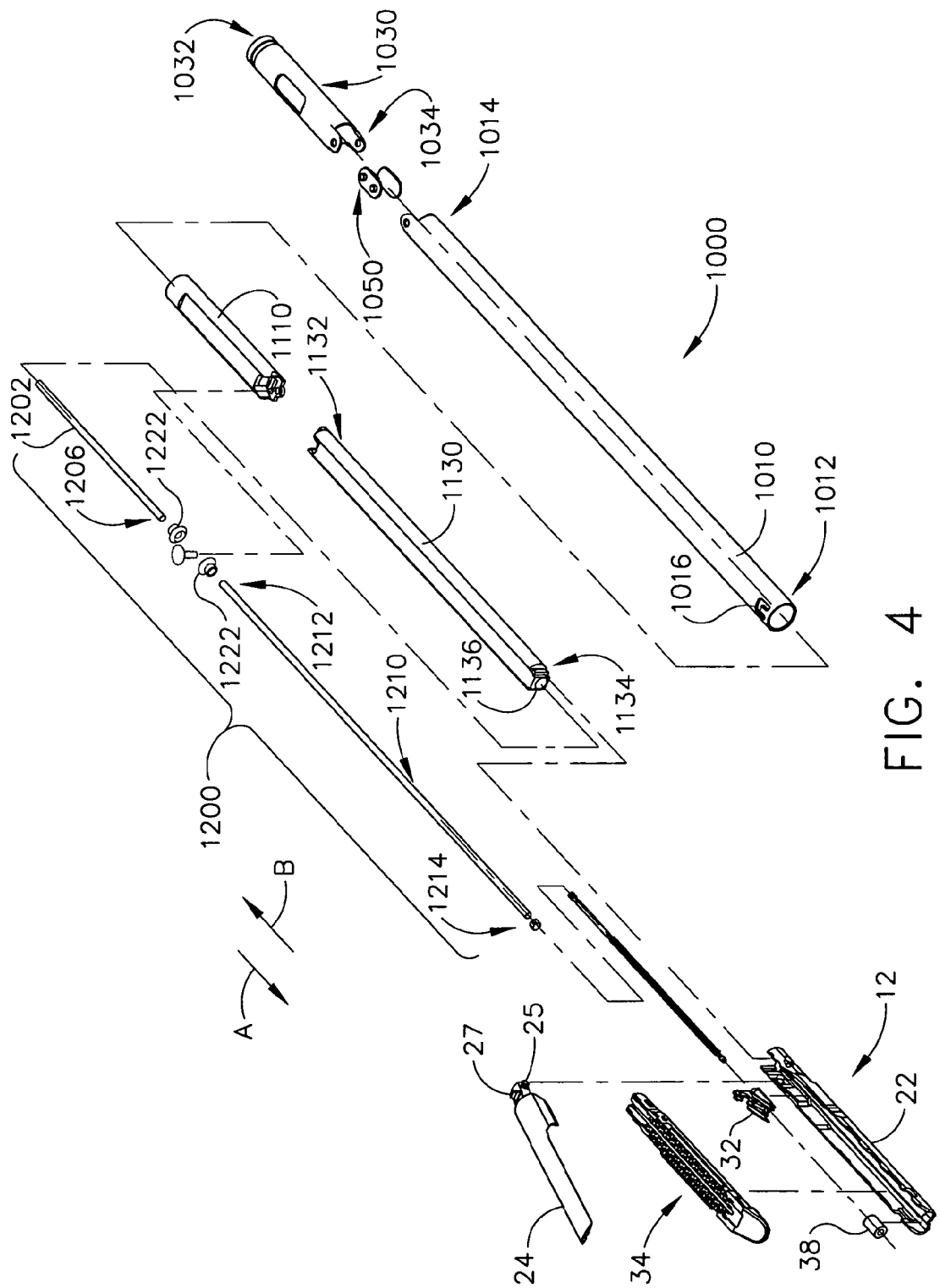
FIG. 4 is another exploded assembly view showing an end effector, drive shaft assembly and elongated shaft assembly of various embodiments of the present invention.
Figure 6:
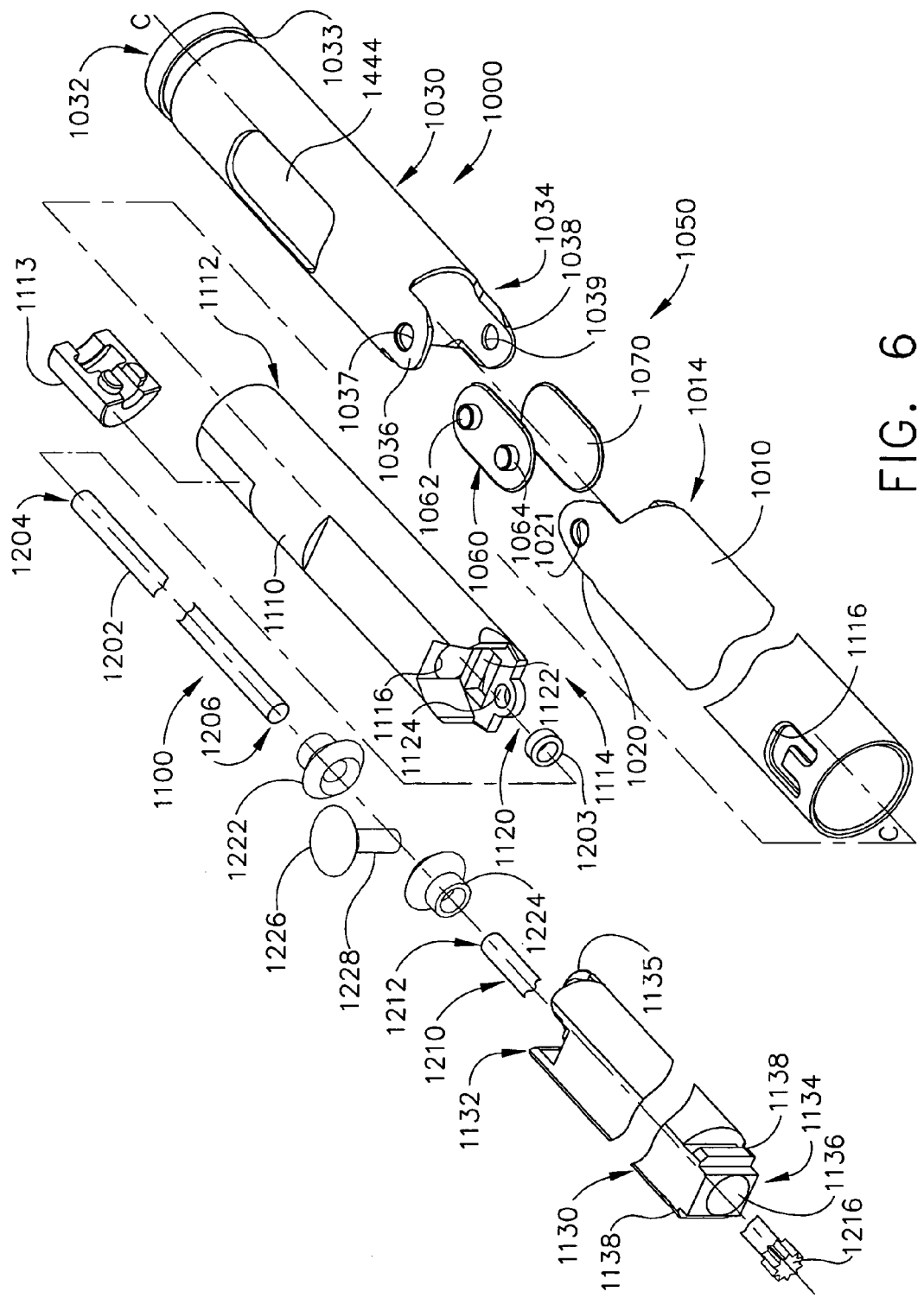
FIG. 6 is an exploded assembly view of an elongated shaft assembly and drive shaft assembly of various embodiments of the present invention.
Figure 7:
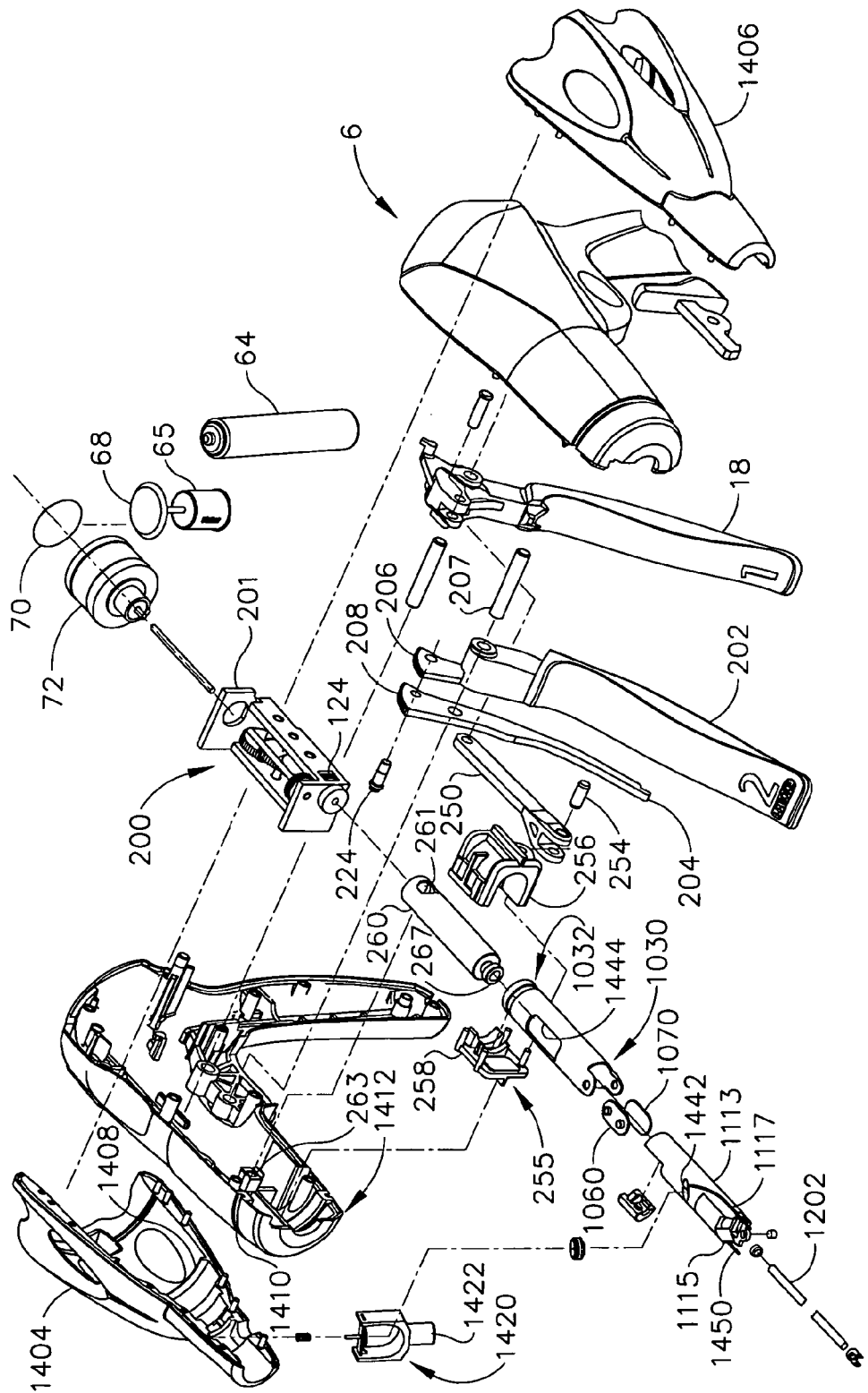
FIG. 7 is an exploded assembly view of a control handle of various embodiments of the present invention.

FIG. 4 is an exploded assembly view of an elongated closure tube assembly 1000, a drive shaft assembly 1200 and an end effector 12 of one embodiment of the present invention. FIG. 5 is a cross-sectional view of a cartridge 34 and distal portions of the elongated shaft assembly and the drive shaft assembly. FIG. 6 is another exploded assembly view of the elongated closure tube assembly 1000 and drive shaft assembly 1200. FIG. 7 illustrates the interface between the elongated closure tube assembly 1000 and the control handle 6. Turning to FIGS. 4 and 5, it can be seen that one embodiment of an elongated closure tube assembly 1000 includes a distal closure tube segment 1010 that has a "second" distal end 1012 and a "second" proximal end 1014.

In various embodiments, the distal closure tube segment 1010 has a U-shaped window 1016 in its distal end 1012. Such U-shaped window 1016 is adapted to engage an upstanding closure tab 27 formed on the anvil 24. See FIG. 4. Thus, when the distal closure tube segment 1010 is moved in the distal direction (arrow "A"), it contacts the closure tab 27 and causes the anvil 24 to pivot to a closed position. When the distal closure tube segment 1010 is moved in the proximal direction (arrow "B") it contacts the closure tab 27 and causes the anvil 24 to pivot to an open position (away from the channel 22).

As can be seen in FIGS. 4 and 6, the elongated closure tube assembly 1000 further includes a proximal closure tube segment 1030 that has a proximal end 1032 and a distal end 1034. The proximal end 1032 of the proximal closure tube segment 1030 is articulatably coupled to the distal end 1014 of the distal closure tube segment 1010 by an articulation joint generally designated as 1050. More specifically and with reference to FIGS. 5A, 5B and 6, articulation joint 1050 comprises in various embodiments a first upper tab 1036 protruding from the distal end 1034 of the proximal closure tube segment 1030 and a first lower tab 1038 protruding from the distal end 1034 of the proximal closure tube segment 1030 in spaced relation to the first upper tab 1036. The first upper tab 1036 has a first upper pivot hole 1037 therethrough and the first lower tab 1038 has a first lower pivot hole 1039 therethrough that is coaxially aligned with the first upper hole 1037 in various embodiments. Similarly, the proximal end 1014 of the proximal shaft segment 1010 has a second upper tab 1020 protruding therefrom and a second lower tab 1022 protruding therefrom in spaced relation to the second upper tab 1020. The second upper tab 1020 has a second upper pivot hole 1021 therethrough and the second lower tab 1022 has a second lower pivot hole 1023 therethrough that is substantially coaxially aligned with the second upper pivot hole 1021. See FIG. 5B.

In various embodiments, the articulation joint 1050 further includes an upper double pivot link 1060 that has a first upper pin 1062 and a second upper pin 1064 protruding therefrom. The first upper pin 1062 is sized to be pivotally received in the first upper pivot hole 1037 and the second upper pin 1064 is sized to be pivotally received in the second upper pivot hole 1021. The upper double pivot link 1060 is retained in position between the proximal end 1014 of the distal closure tube segment 1010 and the distal end 1034 of the proximal closure tube segment 1030 by the proximal spine tube segment 1100 and the distal spine tube segment 1130. The articulation joint 1050 further includes a lower double pivot link 1070 that has a first lower pin 1072 and a second lower pin 1074 protruding therefrom. The first lower pin 1072 is sized to be pivotally received within the first lower pivot hole 1039 and the second lower pin 1074 is sized to be pivotally received in the second lower pivot hole 1023. See FIG. 5B. The lower double pivot link 1070 is retained in position between the proximal end 1014 of the distal closure tube segment 1010 and the distal end 1034 of the proximal closure tube segment 1030 by the proximal spine tube segment 1100 and the distal spine tube segment 1130.

When the upper double pivot link 1060 and the lower double pivot link 1070 are attached to the proximal end 1014 of the distal closure tube segment 1010 and the distal end 1034 of the proximal closure tube segment 1030, the first upper pin 1062 and the first lower pin 1072 are coaxially aligned along a first pivot axis D-D that, in various embodiments, may be substantially transverse to an elongated shaft axis C-C that extends through the elongated closure tube assembly 1000. See FIG. 5A. Likewise, the second upper pivot pin 1064 and the second lower pivot pin 1074 are coaxially aligned along a second pivot axis E-E. In various embodiments, the second pivot axis E-E is substantially transverse to the elongated shaft axis C-C and substantially parallel to the first pivot axis D-D. The reader will appreciate that such arrangement permits the proximal closure tube segment 1030 to pivot relative to the distal closure tube segment 1010 about pivot axes D-D and E-E.

As can be seen in FIGS. 6 and 7, the proximal end 1032 of the proximal closure tube segment 1030 has an attachment groove formed around its circumference to enable it to be coupled to a carriage assembly 255 that is supported within the control handle 6 for imparting axial travel of the shaft assembly 1000 in the distal and proximal directions A, B respectively, as will be discussed in further detail below.

Various embodiments of the present invention further include an elongated spine tube assembly, generally designated as 1100 that extends through the elongated closure tube assembly 1000 to support various components of the drive shaft assembly 1200 therein. In various embodiments, the elongated spine tube assembly 1100 comprises a proximal spine tube segment 1110 that has a proximal end 1112 and a distal end 1114. The proximal end 1112 is adapted to be coupled to an attachment bar 260 located within the control handle 6 which will be discussed in further detail below.

As can be seen in FIG. 6, the distal end 1114 of the proximal spine tube segment 1110 has a lower pivot tab 1120 protruding therefrom, the purpose of which will be discussed in further detail below. As can also be seen in FIG. 6, the proximal spine tube segment 1110 has a first axially extending drive shaft hole 1116 extending therethrough for receiving a portion of the drive shaft assembly 1200 therein as will also be further discussed below.

The elongated spine assembly 1100 also includes a distal spine tube segment 1130 that has a proximal end 1132 and a distal end 1134. The distal spine tube segment 1130 has an axially extending drive shaft hole 1136 therethrough. The distal end 1134 of the distal spine tube segment 1130 is also constructed for attachment to the channel 22. In one embodiment, for example, the distal end 1134 of the distal spine tube segment 1130 may be formed with a pair of attachment columns 1138 that are adapted to be retainingly engaged in slots 29 formed in an end of the channel 22. See FIG. 3. The attachment columns 1138 may be retained within the slots 29 due to the distal spine segment 1130 being contained within the distal closure tube segment 1010 which forces both the channel 22 and the distal spine segment 1130 to always have the same centerline and such that the distal end 1134 of the proximal spine tube segment 1130 is rigidly coupled to the channel 22. The reader will understand that the elongated spine tube assembly 1100 is sized relative to the elongated closure tube assembly 1000 such that the elongated closure tube assembly 1000 can freely move axially thereon.

As can be seen in FIGS. 4-6, the drive shaft assembly 1200 is operably supported within the elongated spine tube assembly 1100 which is supported within the elongated closure tube assembly 1000. In various embodiments, the drive shaft assembly 1200 comprises proximate drive shaft portion 1202, a drive shaft articulation joint 1220 and a distal drive shaft portion 1210. The proximal drive shaft portion 1202 is sized to extend through the elongated drive shaft hole 1116 in the proximal spine tube segment 1110 and may be rotatably supported therein by a bearing 1203. The proximal drive shaft portion 1202 has a proximal end 1204 and a distal end 1206.

The distal drive shaft portion 1210 is sized to extend through the drive shaft hole 1136 in the distal spine tube segment 1130 and be rotatably supported therein by a bearing 1207. See FIG. 5B. The distal drive shaft 1210 has a proximal end 1212 and a distal end 1214. The distal end 1214 has a drive gear 1216 attached thereto that is in meshing engagement with a gear 56 attached to the helical screw shaft 36. See FIG. 5A.

In one embodiment depicted in FIGS. 4-6, the drive shaft articulation joint 1220 comprises a first proximal bevel gear 1222 attached to the distal end 1206 of the proximal drive shaft portion 1202. A clearance opening 1122 is provided through the first lower pivot tab 1120 to enable the first proximal bevel gear 1222 to rotate relative thereto. This embodiment of the drive shaft articulation joint 1220 further includes a first distal bevel gear 1224 attached to the proximal end 1212 of the distal drive shaft portion 1210. An opening 1137 is provided through the second lower pivot tab 1135 protruding from the proximal end 1132 of the distal spine tube segment 1130 to enable the first distal bevel gear 1224 to freely rotate relative to the second lower pivot tab 1135. Also in this embodiment, the drive shaft articulation joint 1220 comprises a central bevel gear 1226 that is mounted to a shaft 1228 that is pivotally mounted in pivot hole 1124 formed in the first lower pivot tab 1120 and a pivot hole 1124' formed in the second lower pivot tab 1135. See FIG. 5B. The reader will appreciate that the shaft 1228 serves to pivotally couple the distal end 1114 of the proximal spine tube segment 1110 to the proximal end 1132 of the distal spine tube segment 1130. The central bevel gear 1226 is supported in meshing engagement with the first distal bevel gear 1224 and the first proximal bevel gear 1222 such that rotation of the proximal drive shaft portion 1202 is transmitted to the distal drive shaft portion 1210 through the drive shaft articulation joint 1220 while facilitating articulatable movement of the drive shaft assembly 1200 when the proximal closure tube segment 1030 of the elongated closure tube assembly 1000 is articulated relative to the distal closure tube segment 1010 thereof.

Figure 8:
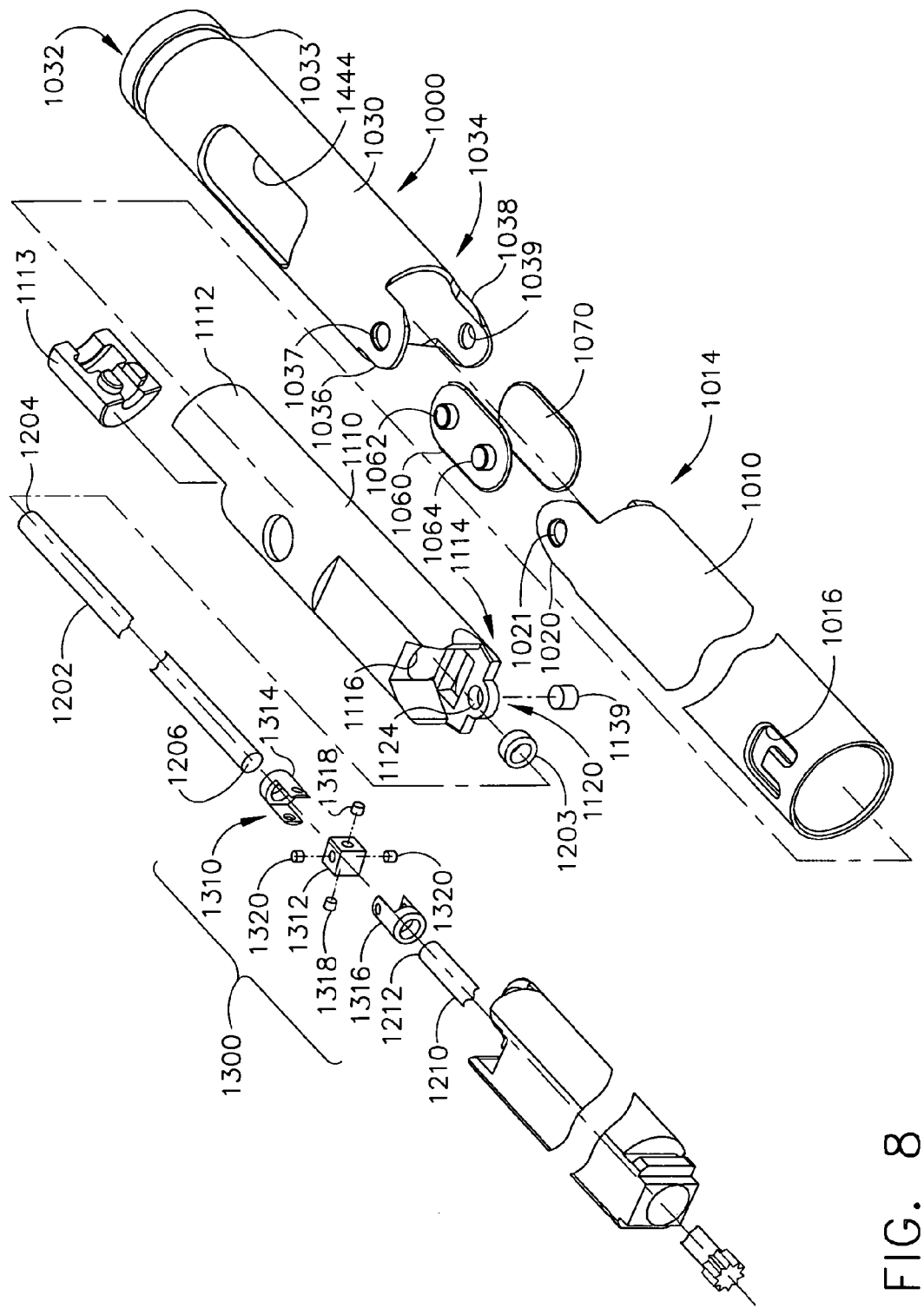
FIG. 8, is an exploded perspective view of an elongated shaft assembly and a drive shaft assembly of another embodiment of the present invention.
Figure 9:
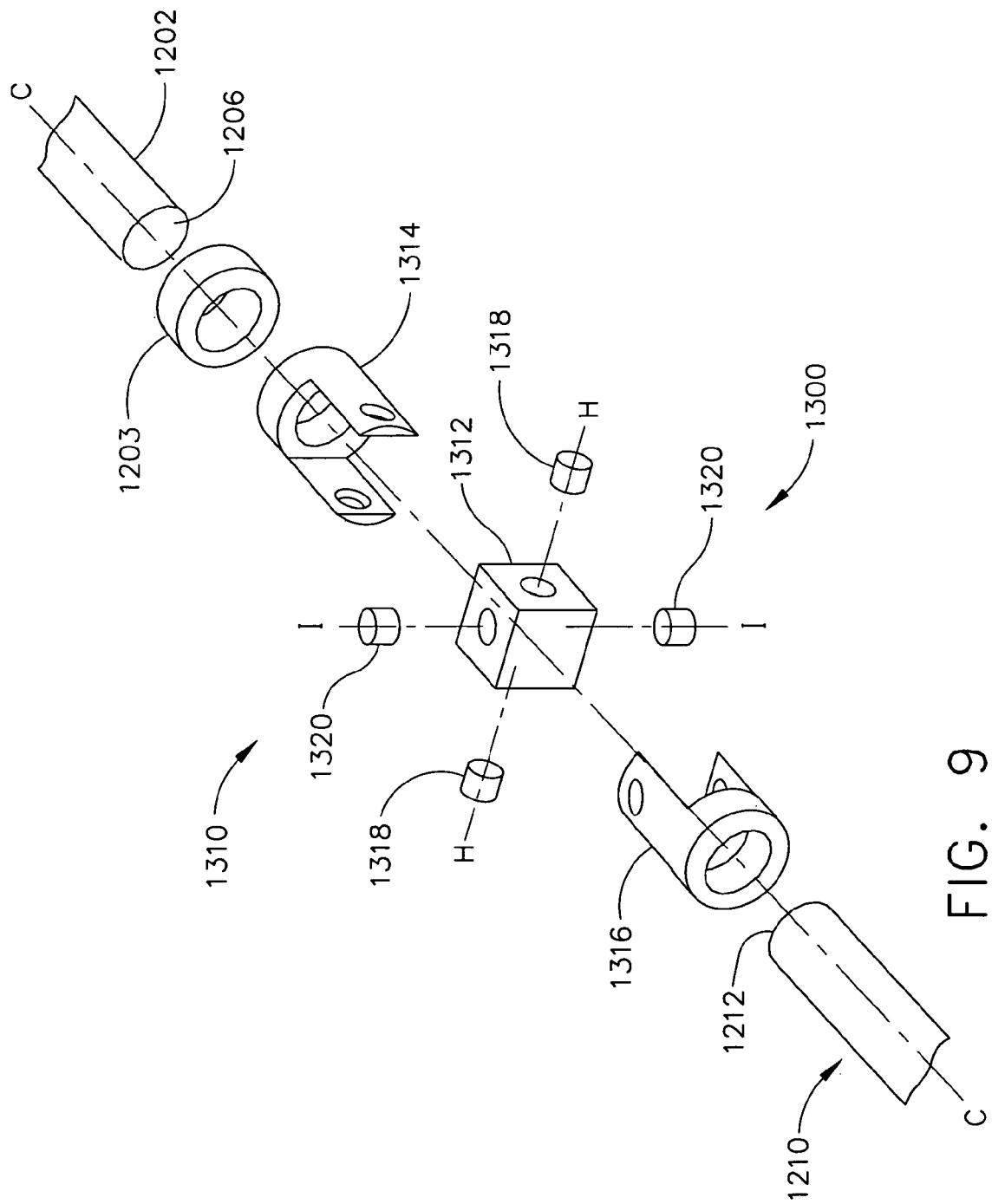
FIG. 9 is an exploded assembly view of the articulation joint of the drive shaft assembly depicted in FIG. 8.
Figure 10:
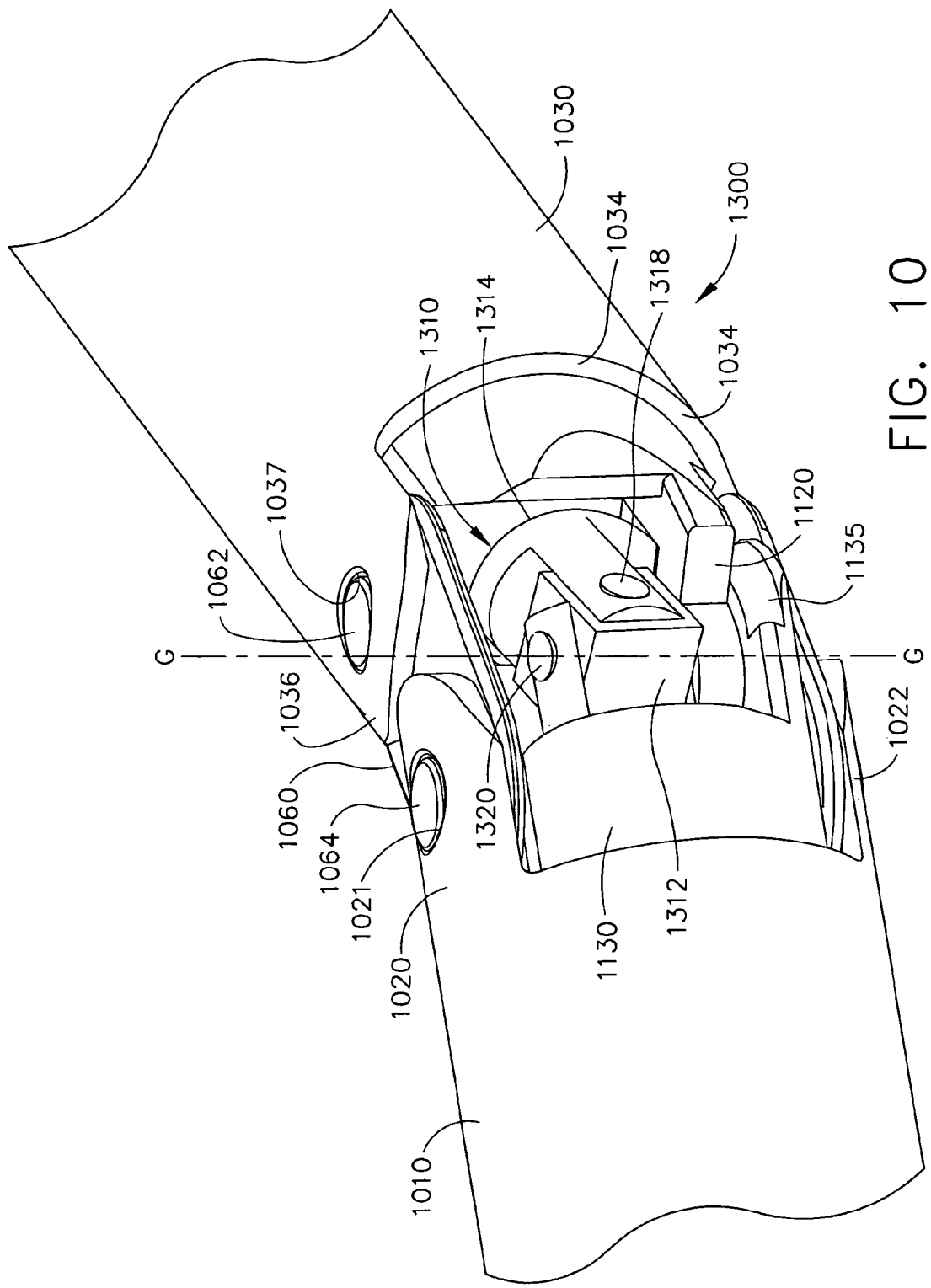
FIG. 10 is a partial perspective view of the drive shaft articulation joint and proximal and distal drive shaft portions of various embodiments of the present invention.

FIGS. 8-10 illustrate an alternative drive shaft articulation joint 1300 that may be employed to facilitate substantial universal travel of the proximal drive shaft portion 1202 relative to the distal drive shaft portion 1210. As can be seen in Figure, the elongated closure tube assembly 1000 and the elongated spine tube assembly 1100 may be constructed and operate in the manner described above. Turning to FIGS. 8 and 10, in this embodiment, the first lower pivot tab 1120 on the proximal spine tube segment 1110 is pivotally coupled to the second lower pivot tab 1135 on the distal spine tube segment 1130 by a vertical pivot pin 1139. More specifically, the pivot pin 1139 is pivotally received with pivot hole 1124 in the first lower pivot tab 1120 and another pivot hole (not shown) in the second lower pivot tab 1135 to facilitate pivotal travel of the proximal spine tube segment 1110 relative to the distal spine tube segment 1130 about a pivot axis G-G which is defined by pivot pin 1139.

Also in this embodiment, the drive shaft articulation joint 1300 comprises universal joint 1310 that includes a central joint body 1312 that is pivotally coupled to a proximal yoke member 1314 and a distal yoke member 1316. As indicated in the above description, the distal end 1206 of the proximal drive shaft portion 1202 is rotatably supported in the proximal spine tube segment 1110 by a bearing 1203. The proximal yoke assembly 1314 is attached to the distal end 1206 of the proximal drive shaft portion 1202 and is constructed to pivotally receive a pair of proximal pivot pins 1318 that are attached to or otherwise formed in the central joint body 1312. Such proximal pivot pins 1318 facilitate pivotal travel of the central joint body 1312 relative to the proximal drive shaft portion 1202 about a proximal pivot axis H-H which may be substantially transverse to the elongated shaft axis C-C.

Similarly, the distal yoke member 1316 is attached to the proximal end 1212 of the distal drive shaft portion 1210. The distal yoke member 1316 is adapted to pivotally receive a pair of distal pivot pins 1320 attached to or otherwise formed in the central joint body 1312. Such distal pivot pins 1320 facilitate pivotal travel about a distal pivot axis I-I that is substantially transverse to the proximal pivot axis H-H and the elongated shaft axis C-C.

FIGS. 11A and 11B, illustrate yet another drive shaft articulation arrangement of the present invention that may be employed to facilitate substantial universal travel of the proximal drive shaft portion 1202 relative to the distal drive shaft portion 1210. In this embodiment, a torsion cable 1390 is attached between the proximal end 1212 of the distal drive shaft portion 1210 and the distal end 1206 of the proximal drive shaft portion 1210 to permit the proximal drive shaft portion 1202 to articulate relative to the distal drive shaft portion 1210.

Components of an exemplary closure system for closing (or clamping) the anvil 24 of the end effector 12 by retracting the closure trigger 18 are also shown in FIG. 7. In the illustrated embodiment, the closure system includes a yoke 250 connected to the closure trigger 18. A pivot pin 252 is inserted through aligned openings in both the closure trigger 18 and the yoke 250 such that they both rotate about the same point. The distal end of the yoke 250 is connected, via a pin 254, to a first portion 256 of the closure bracket 255. The first closure bracket portion 256 connects to a second closure bracket portion 258. Collectively, the closure bracket 255 defines an opening in which the proximal end 1032 of the proximal closure tube segment 1030 is seated and held such that longitudinal movement of the closure bracket 255 causes longitudinal motion by the proximal closure tube segment 1030 (and ultimately the elongated closure tube assembly 1000). The instrument 10 also includes a closure rod 260 disposed inside the proximal closure tube 1030. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximal closure tube segment 1030 is capable of moving longitudinally relative to the closure rod 260. The closure rod 260 may also include a distal collar 267 that fits into a cavity 1111 in the proximal end 1112 of the proximal spine tube segment 1110 and is retained therein by a cap 1113 (see FIGS. 6-8 and 12).

In operation, when the yoke 250 rotates due to retraction of the closure trigger 18, the closure bracket 255 causes the proximal closure tube segment 1030 to move proximately (i.e., toward the handle end of the instrument 10), which causes the distal closure tube segment 1010 to move proximately. Because the tab 27 extends through the window 45 of the distal closure tube segment 1010, the tab 27 causes the anvil to open when the distal closure tube moves proximately. When the closure trigger 18 is unlocked from the locked position, the proximal closure tube segment 1030 is caused to slide distally, which causes the distal closure tube segment 1010 to slide distally. The distal closure tube segment 1010 forces the anvil 24 closed by driving it distally by interacting with a closure lip 27' that is distal to tab 27. Further closure is accomplished since the distal movement of the anvil 24 forces the anvil pin 25 to move distally up the cam slot 23 in the channel 22, creating compressive loads through this camming action and the hoop constraint of distal closure tube segment 1010 around the two parts. In that way, by retracting and locking the closure trigger 18, an operator may clamp tissue between the anvil 24 and the cartridge 34 mounted within the channel 22, and may unclamp the tissue following the cutting/stapling operation by unlocking the closure trigger 20 from the locked position.

As shown in FIG. 2, the end effector 12 and the distal end 1012 of the distal closure tube segment are sized to be inserted through a trocar assembly 900 into the patient. Such trocar assemblies are known in the art and therefore, its construction and operation are not discussed in detail herein. For example, U.S. Pat. No. 6,017,356 to Frederick et al., entitled METHOD FOR USING A TROCAR FOR PENETRATION AND SKIN INCISION, the disclosure of which is herein incorporated by reference in its entirety discloses various trocar assemblies. The reader will, of course, appreciate, however, that the various embodiments of the present invention may be effectively employed with a variety of different trocar, cannula, etc. arrangements without departing from the spirit and scope of the present invention. Therefore, the various embodiments of the present invention and their equivalent structures should not in any way be limited to use with the specific type of trocar described herein by way of example.

As can be seen in FIG. 2, the trocar assembly 900 includes a cannula assembly 902 that is attached to a cannula housing 904. The end effector 12 and the distal end 1012 of the distal closure tube segment 1010 are sized to be inserted through the cannula housing 904 and cannula assembly 902 into the patient. Depend upon the procedure to be performed and the location of the organs to be operated on, various lengths of the distal closure tube segment 1010 may be inserted into the trocar 900. That portion of the closure tube assembly 1000 that is adapted to be inserted into the trocar 900 is referred to herein as the "distal portion" 1002 and could conceivably comprise substantially all of the distal closure tube segment 1010 up to the proximal end 1014 such that the articulation joint 1050 remains external to the trocar 900 and is operable to permit the surgeon or clinician to articulate the handle 6 relative to the distal portion 1002 in the trocar. The reader will further appreciate that the distal portion 1002 may comprise somewhat less than the entire length of the distal closure tube segment 1010. Thus, the various embodiments of the present invention enable the surgeon to articulate the handle 6 of the device 10 to a more ergonomically comfortable position during the operation about the pivot links 1060 and 1070.

Various embodiments of the present invention may also be provided with a locking system 1400 that would enable the surgeon to lock the handle in a desired position relative to the portion of the device inserted into the trocar 900. More specifically and with reference to FIGS. 12-15, one locking system embodiment may by supported within a rotatable housing assembly 1402 that is attached to the forward portion 7 of the handle 6. In various embodiments, the housing assembly 1402 may comprise a first housing segment 1404 and a second housing segment 1406 that are constructed to fit together to form the housing 1402. The housing segments 1404, 1406 may be formed from plastic and be constructed to be retained together by snapping arrangements and/or adhesive, screws, etc. As can be seen in FIG. 7, housing segment 1404 has an ring segment 1408 formed therein that is adapted to mate with a similar ring segment (not shown) that is formed in the interior of housing segment 1406 to form an annular ring assembly sized to be received in an annular groove 1410 formed in the forward portion 1412 of the handle 6. Such arrangement enables the housing assembly 1402 to be coupled to the handle 6 and be freely rotatable relative thereto.

As can be seen in FIGS. 12 and 13, the housing assembly 1402 houses an actuator assembly in the form of a push button assembly 1420. In various embodiments, the push button assembly 1420 may have a push button portion 1422 and a yoke portion 1424 attached thereto. As can be seen in FIG. 13, the push button portion 1422 is adapted to protrude through a hole 1414 formed in the housing 1402 and the yoke portion 1424 is slidably supported within a cavity 1416 formed in the housing 1402. The yoke portion 1424 has a pair of legs 1426, 1428 that are separated by an end brace 1430. As can also be seen in FIG. 13, the proximal closure tube segment 1030 is received between the legs 1426, 1428 such that the proximal closure tube segment 1030 can move axially therebetween on the proximal spine tube segment 1110. As can be seen in that Figure, the proximal drive shaft portion 1202 is movably supported within the axially extending hole 1116 in the proximal spin tube segment 1110.

As can be seen in FIGS. 12 and 13, a cable wheel 1440 is rotatably supported within a wheel cavity 1442 provided in the proximal spine tube segment 1110 and extends through an opening 1444 in the proximal closure tube segment 1030. Such arrangement permits the cable wheel 1440 to freely rotate in wheel cavity 1442. Cable wheel 1440 has an upper cable-receiving groove 1446 and a lower cable-receiving groove 1448 formed around its perimeter. A right tension cable 1450 is received within the lower cable-receiving groove and a left tension cable 1460 is received within the upper cable-receiving groove. The right tension cable 1450 is received within a first groove 1115 formed in the outer surface 1113 of the proximal spine tube segment 1110 and the left tension cable 1460 is received within a second groove 1117 formed in the outer surface 1113 of the proximal spine tube segment 1110. See FIG. 16. The right tension cable 1440 has a distal end 1442 that is attached to the right side of the proximal end 1132 of the distal spine tube segment 1130 and a proximal end that is attached to the cable wheel 1440. Likewise, the left tension cable 1460 has a distal end 1462 that is attached to the left side of the proximal end 1132 of the distal spine tube segment 1130 and a proximal end that is attached to the cable wheel 1440. See FIG. 16. Thus, when the proximal closure tube segment 1030 and handle 6 is articulated relative to the distal closure tube segment 1010, the cable wheel 1440 is caused to rotate within the cable wheel cavity 1442 by virtue of tension cables 1450, 1460.

Various embodiments of the locking assembly also include a disengagable gear assembly 1470 for locking the cable wheel 1440 which ultimately prevents the proximal closure tube segment 1030 (and handle 6) from articulating relative to the distal closure tube segment 1010. More specifically and with reference to FIGS. 13-15, the disengagable gear assembly 1470 comprises a first gear 1472 that is attached to the cross brace 1430 on the push button assembly 1420. A second mating gear 1474 is attached to the end of the cable wheel 1440 and is adapted to be selectively meshed with the first fixed gear 1472. The first gear 1472 is biased into meshing engagement by a locking spring 1476 that is journaled on a retainer prong 1478 protruding from the cross brace 1430 and received within a spring cavity formed within the housing assembly. Spring 1476 serves to bias the first and second gears 1472, 1474 into meshing engagement with each other (e.g., in the "K" direction). See Figure. When the user pushes the push button 1422 in the "L" direction, the first gear 1472 is moved out of meshing engagement with the second gear 1474 to thereby permit the second gear 1474 and cable wheel 1440 to which it is attached rotate.

The locking assembly 1420 may operate in the following manner. When the first and second gears 1472, 1474 are in meshing engagement as shown in FIGS. 13 and 14, the cable wheel 1440 cannot rotate and the right cable 1450 and left cable 1460 prevent the proximal closure tube 1030 (and handle) from articulating about the double pivot pins 1060, 1070 relative to the distal closure tube assembly 1010. To unlock the articulation joint 1050, the user pushes the push button 1422 inwardly to cause the first gear 1472 to disengage the second gear 1474. The user can then articulate the proximal closure tube segment 1030 (and handle 6) relative to the distal closure tube segment 1010. After the surgeon has articulated the handle 6 to the desired position, the push button 1422 is released and the first gear 1472 is biased into meshing engagement with the second gear 1474 to lock the articulation joint 1050 in that position. To provide the user with further flexibility, it will be understood that the housing assembly 1402 and the proximal closure tube segment 1030 and locking assembly 1420 may be rotated relative to the handle 6 to provide the user with additional flexibility.

FIGS. 17-22 illustrate one aspect of a motorized drive arrangement for powering the endocutter 10. Various other motorized drive arrangements such as those copending U.S. patent applications which have been herein incorporated by reference above in their entirety could also be effectively employed in various embodiments. As was also mentioned before, however, the unique and novel aspects of the present invention may also be practiced in connection with mechanically actuated surgical devices, without departing from the spirit and scope of the present invention. As can be seen in FIG. 7 and FIGS. 17-22, one exemplary embodiment includes a gear box assembly 200 including a number of gears disposed in a frame 201, wherein the gears are connected between the planetary gear 72 and the pinion gear 124 at the proximal end 1204 of the proximal drive shaft portion 1202. As explained further below, the gear box assembly 200 provides feedback to the user via the firing trigger 20 regarding the deployment of the end effector 12. Also, the user may provide power to the system via the gear box assembly 200 to assist the deployment of the end effector 12.

In the illustrated embodiment, the firing trigger 18 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 209 may be inserted through openings in the firing trigger pieces 202, 204 and may be the point about which the firing trigger 20 rotates. In addition, a spring 222 may bias the firing trigger 20 to rotate in a CCW direction. The spring 222 may have a distal end connected to a pin 224 that is connected to the pieces 202, 204 of the firing trigger 18. The proximate end of the spring 222 may be connected to one of the handle exterior lower side pieces 59, 60.

In the illustrated embodiment, both the main body portion 202 and the stiffening portion 204 includes gear portions 206, 208 (respectively) at their upper end portions. The gear portions 206, 208 engage a gear in the gear box assembly 200, as explained below, to drive the main drive shaft 48 and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 18. In addition, the first gear 210 engages a smaller second gear 212, the smaller second gear 212 being coaxial with a large third gear 214. The third gear 214 engages a smaller fourth gear 216, the smaller fourth gear being coaxial with a fifth gear 218. The fifth gear 218 is a 90° bevel gear that engages a mating 90° bevel gear 220 (best shown in FIG. 22) that is connected to the pinion gear 124 that drives the main drive shaft 48.

In operation, when the user retracts the firing trigger 18, a sensor (not shown) is activated, which may provide a signal to the motor 65 to rotate at a rate proportional to the extent or force with which the operator is retracting the firing trigger 18. This causes the motor 65 to rotate at a speed proportional to the signal from the sensor. The sensor could be located in the handle 6 such that it is depressed when the firing trigger 18 is retracted. Also, instead of a proportional-type sensor, an on/off type sensor may be used.

Rotation of the motor 65 causes the bevel gears 66, 70 to rotate, which causes the planetary gear 72 to rotate, which causes, via the drive shaft 76, the ring gear 122 to rotate. The ring gear 122 meshes with the pinion gear 124, which is connected to the proximal drive shaft portion 1202. Thus, rotation of the pinion gear 124 drives the drive, shaft portion 1202, which transmits through the drive shaft articulation joint 1220 to the distal drive shaft portion 1210 which transmits to the shaft 36 through gears 1216 and 56 to thereby cause actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particularly, to the forward speed of the motor 65. Similarly, when the operator releases the firing trigger 20 after the cutting/stapling operation so that it can return to its original position, the user will experience a CW rotation force from the firing trigger 18 that is generally proportional to the reverse speed of the motor 65. The reader will appreciate however, that the unique and novel articulating handle arrangement of the present invention may be effectively employed in connection with a myriad of other powered endoscopic instruments, regardless of the particular handle configuration and/or method of transmitting power to the drive shaft assembly. Accordingly, the protections afforded to the various embodiments of the present invention should not be limited to the particular, motor/handle arrangement disclosed herein.

It will be appreciated from the foregoing discussion, that various embodiments of the present invention represent vast improvements over prior endoscopic instruments. In particular, various embodiments of the present invention permit the surgeon or clinician to effectively position the handle portion of the instrument relative to the other portion of the instrument that is inserted into the patient such that the handle is in a more ergonomically comfortable position and the position of the handle is not dictated by the position of the end effector.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument, comprising:
   an end effector sized to be inserted through a trocar, the trocar having an insertion end portion and a proximal end portion;
   an elongated shaft assembly coupled to said end effector, said elongated shaft assembly defining a longitudinal axis, said elongated shaft assembly having a distal portion adjacent to said end effector for insertion into the trocar with said end effector, a proximal portion remote from said distal portion such that said proximal portion protrudes from the trocar when the end effector and distal portion are inserted therethrough, and a midpoint;
   a control handle articulatably coupled to said proximal portion of said elongated shaft assembly;
   a rotary drive shaft assembly configured to actuate said end effector, wherein said rotary drive shaft assembly is rotatable along said longitudinal axis with respect to said control handle and said end effector, said drive shaft assembly comprising:
   a non-contourable distal drive shaft portion operably coupled to an actuator shaft in said end effector;
      a non-contourable proximal drive shaft portion operably coupled to a motor supported in said control handle; and
      a non-translatable articulation joint comprising a torsion cable coupled between said non-contourable distal drive shaft portion and said non-contourable proximal drive shaft portion to enable said non-contourable proximal drive shaft portion to articulate relative to said non-contourable distal drive shaft portion when said handle is articulated relative to said elongated shaft assembly, wherein said non-translatable articulation joint is positioned proximally with respect to said midpoint of said elongated shaft assembly and proximally with respect to the proximal end of the trocar, and wherein said non-translatable articulation joint is configured to permit said control handle to pivot with respect to said non-contourable distal drive shaft portion.

2. The surgical instrument of claim 1 wherein said proximal portion of said elongated shaft assembly comprises:
   a proximal shaft segment having a first distal end and a first proximal end, said first proximal end coupled to said control handle; and
   a distal shaft segment having a second distal end portion coupled to said end effector and a second proximal end portion sized to protrude out of the trocar when said end effector is inserted through the trocar, wherein said non-translatable articulation joint is attached to said first distal end of said proximal shaft segment and said second proximal end portion of said distal shaft segment.

3. The surgical instrument of claim 2 wherein said proximal shaft segment is rotatably coupled to said control handle for selective rotation relative to said control handle.

4. The surgical instrument of claim 2 wherein said non-translatable articulation joint comprises:
   a first upper tab protruding from said first distal end of said proximal shaft segment;
   a first lower tab protruding from said first distal end of said proximal shaft segment and in spaced relation to said first lower tab;
   a second upper tab protruding from said second proximal end portion of said distal shaft segment;
   a second lower tab protruding from said second proximal end portion of said distal shaft segment in spaced relation to said second upper tab;
   an upper double pivot link sized to span between said first and second upper tabs, said upper double pivot link having a first upper pin pivotally coupled to said first upper tab and a second upper pivot pin pivotally coupled to said second upper tab; and
   a lower double pivot link sized to span between said first and second lower tabs, said lower double pivot link having a first lower pin pivotally coupled to said first lower tab and a second lower pin pivotally coupled to said second lower tab.

5. The surgical instrument of claim 4 wherein said elongated shaft assembly has an elongated shaft axis and wherein said non-translatable articulation joint is constructed to permit said distal shaft segment to pivot about at least one pivot axis relative to said proximal shaft segment.

6. The surgical instrument of claim 5 wherein said first upper pin and said first lower pin are aligned to define a first pivot axis transverse to said elongated shaft axis and wherein said second upper pin and said second lower pin are aligned to define a second pivot axis transverse to said elongated shaft axis.

7. The surgical instrument of claim 2 wherein said torsion cable is located within said non-translatable articulation joint coupling said proximal shaft segment to said distal shaft segment.

8. The surgical instrument of claim 7 further comprising:
   a proximal spine tube segment attached to said control handle and received in said proximal shaft segment, said proximal spine tube segment operably supporting a portion of said non-contourable proximal drive shaft portion therein; and
   a distal spine tube segment pivotally coupled to said proximal spine tube segment and supported in said distal shaft segment and attached to said end effector, said distal spine tube segment operably supporting said non-contourable distal drive shaft portion therein.

9. The surgical instrument of claim 8 wherein said non-translatable articulation joint comprises:
- a central bevel gear rotatably affixed to a distal end of said proximal spine tube segment and supported between a proximal end of said non-contourable distal drive shaft portion and a distal end of said non-contourable proximal drive shaft portion;
- a first distal bevel gear coupled to said proximal end of said non-contourable distal drive shaft portion and in meshing engagement with said central bevel gear; and
- a first proximal bevel gear coupled to said distal end of said non-contourable proximal drive shaft portion and in meshing engagement with said central bevel gear.

10. The surgical instrument of claim 8 further comprising a locking system cooperating with said elongated shaft assembly and control handle to selectively lock said control handle in desired positions relative to said elongated shaft assembly.

11. The surgical instrument of claim 10 wherein said locking system comprises an actuator assembly operably supported on said instrument and movable between a locked position and an unlocked position, said actuator assembly communicating with said distal spine segment such that when said actuator assembly is in said locked position, said proximal spine tube assembly is prevented from articulating relative to said distal spine tube assembly and when said actuator assembly is in said unlocked position, said proximal spine tube segment can articulate with respect to said distal spine tube segment.

12. The surgical instrument of claim 11 wherein said actuator assembly comprises:
- a push button assembly movably supported within a housing supported on the control handle, said push button assembly comprising:
  - a push button portion;
  - a yoke portion attached to said push button portion, said yoke portion supporting said proximal end of said proximal shaft segment therein, said proximal end of said proximal shaft segment supporting said proximal spine tube segment therein, said yoke portion having a first gear attached thereto;
- a cable wheel rotatably supported in said proximal spine tube segment that is supported within said proximal end of said proximal shaft segment supported within said yoke portion, said cable wheel having a second gear attached thereto for selective meshing engagement with said first gear;
- a right tension cable attached to said cable wheel and a right side of a proximal end of said distal spine segment;
- a left tension cable attached to said cable wheel and a left side of said proximal end of said distal spine segment; and
- a biaser between said housing and said push button assembly to bias said first gear into meshing engagement with said second gear, when said push button is not activated and to permit said second gear to unmesh with said first gear upon application of an activation force to said push button portion.

13. The surgical instrument of claim 1 wherein said non-translatable articulation joint comprises a universal joint.

14. The surgical instrument of claim 1 wherein said non-translatable articulation joint comprises:
- a central bevel gear rotatably supported between a proximal end of said non-contourable distal drive shaft portion and a distal end of said non-contourable proximal drive shaft portion;
- a first distal bevel gear coupled to said proximal end of said non-contourable distal drive shaft portion and in meshing engagement with said central bevel gear; and
- a first proximal bevel gear coupled to said distal end of said non-contourable proximal drive shaft portion and in meshing engagement with said central bevel gear.

15. The surgical instrument of claim 1 further comprising a locking system cooperating with said elongated shaft assembly and control handle to selectively lock said control handle in desired positions relative to said elongated shaft assembly.

16. The surgical instrument of claim 15 wherein said non-translatable articulation joint comprises:
- a proximal yoke member attached to a distal end of said non-contourable proximal drive shaft portion;
- a distal yoke member attached to a proximal end of said non-contourable distal drive shaft portion; and
- a central joint body pivotally coupled to said proximal and distal yoke members.

17. The surgical instrument of claim 16 wherein said central body member is pivotally pinned to said proximal yoke member for pivotal travel about a proximal pivot axis transverse to an elongated shaft axis and wherein said central body is pivotally pinned to the distal yoke member for pivotal travel about a distal axis transverse to said elongated shaft axis.

18. The surgical instrument of claim 17 wherein said proximal pivot axis is transverse to said distal pivot axis.

19. A surgical instrument, comprising:
- an end effector sized to be inserted through a trocar, the trocar having an insertion end portion and a proximal end portion;
- a elongated shaft assembly coupled to said end effector, said elongated shaft assembly having a distal portion adjacent to said end effector for insertion into the trocar with said end effector, a proximal portion remote from said distal portion such that said proximal portion protrudes from the trocar when the end effector and distal portion are inserted therethrough, and a midpoint; and
- means for controlling said end effector articulatably coupled to said proximal portion of said elongated shaft assembly, said means for controlling comprising a non-contourable distal drive shaft configured to apply at least one rotary control motion to the end effector, said non-contourable distal drive shaft operably coupled to a non-contourable proximal drive shaft by a torsion cable configured to transmit rotary control motions from the non-contourable proximal drive shaft to the non-contourable distal drive shaft while facilitating selective articulation of the non-contourable distal drive shaft relative to the non-contourable proximal drive shaft, wherein said means for controlling said end effector is positioned proximally with respect to said midpoint of said elongated shaft assembly and proximally with respect to the proximal end of the trocar, and wherein said means for controlling said end effector comprise a non-translatable pivot axis.

20. A surgical instrument, comprising:
- an end effector sized to be inserted through a trocar;
- a control handle operably supporting at least one drive motor therein;
- a rigid proximal hollow shaft segment having a first proximal end rotatably coupled to said control handle for selective rotation about an elongated shaft axis and a first distal end;
- a rigid distal hollow shaft segment having a second distal end portion operably coupled to said end effector for selective actuation thereof by axial movement along said elongated shaft axis, said rigid distal hollow shaft segment having a second proximal end portion sized to protrude out of the trocar when said end effector is inserted through the trocar;

a first upper tab protruding from said first distal end of said rigid proximal hollow shaft segment;

a first lower tab protruding from said first distal end of said rigid proximal hollow shaft segment and in spaced relation to said first lower tab;

a second upper tab protruding from said second proximal end of said rigid distal hollow shaft segment;

a second lower tab protruding from said second proximal end of said rigid distal hollow shaft segment in spaced relation to said second upper tab;

an upper double pivot link sized to span between said first and second upper tabs, said upper double pivot link having a first upper pin pivotally coupled to said first upper tab and a second upper pivot pin pivotally coupled to said second upper tab;

a lower double pivot link sized to span between said first and second lower tabs, said lower double pivot link having a first lower pin pivotally coupled to said first lower tab and a second lower pin pivotally coupled to said second lower tab;

a proximal spine segment attached to said control handle and extending through said rigid proximal hollow shaft segment and protruding from said first distal end thereof;

a distal spine segment extending through said rigid distal hollow shaft segment and having a proximal end adjacent a distal end of said proximal spine segment, said distal spine segment having a distal end attached to said end effector and being supported within said rigid distal hollow shaft segment such that said rigid distal hollow shaft segment can be selectively axially moved relative to said distal spine segment;

a non-contourable distal drive shaft portion operably supported in said distal spine segment and being coupled to an actuator shaft in said end effector;

a non-contourable proximal drive shaft portion operably coupled to one of said at least one drive motors in said control handle and operably supported within said proximal spine segment; and a torsion cable coupled between said non-contourable distal drive shaft portion and said non-contourable proximal drive shaft portion to enable said non-contourable proximal drive shaft portion to articulate relative to said non-contourable distal drive shaft portion about a non-translatable pivot axis when said control handle is articulated relative to said distal shaft segment.

21. The surgical instrument of claim 20 further comprising a drive shaft articulation joint, wherein said drive shaft articulation joint comprises:

a central bevel gear rotatably affixed to a distal end of said proximal spine segment and supported between a proximal end of said non-contourable distal drive shaft portion and a distal end of said non-contourable proximal drive shaft portion;

a first distal bevel gear coupled to said proximal end of said non-contourable distal drive shaft portion and in meshing engagement with said central bevel gear; and a first proximal bevel gear coupled to said distal end of said non-contourable proximal drive shaft portion and in meshing engagement with said central bevel gear.

22. The surgical instrument of claim 20 further comprising a non-translatable drive shaft articulation joint, wherein said non-translatable drive shaft articulation joint comprises a universal joint.

23. The surgical instrument of claim 20 further comprising means supported on said instrument for selectively locking said rigid proximal hollow shaft segment in a desired position relative to said rigid distal hollow shaft segment.

24. A surgical instrument, comprising:

an end effector sized and configured to be inserted through a trocar, the trocar comprising an insertion end, a proximal end, and a trocar length extending between the insertion end and the proximal end;

a rotatable drive shaft configured to actuate said end effector, said rotatable drive shaft defining a longitudinal axis, wherein said rotatable drive shaft is rotatable along said longitudinal axis with respect to said end effector, said rotatable drive shaft comprising:

a non-contourable distal end, wherein said end effector extends from said non-contourable distal end; and a non-articulating portion comprising a non-articulating shaft length which is at least as long as the trocar length;

a handle configured to operate said end effector; and a non-translatable articulation joint, wherein said handle is rotatably connected to said shaft about said articulation joint.

* * * * *